US005684137A

United States Patent [19]
Kasina et al.

[11] Patent Number: 5,684,137
[45] Date of Patent: Nov. 4, 1997

[54] S₃N CHELATING COMPOUNDS FOR THE RADIOLABELING OF LIGANDS, ANTI-LIGANDS OR OTHER PROTEINS

[75] Inventors: Sudhakar Kasina, Kirkland; Linda M. Gustavson, Seattle, both of Wash.

[73] Assignee: NeoRx Corporation, Seattle, Wash.

[21] Appl. No.: 393,882

[22] Filed: Feb. 22, 1995

Related U.S. Application Data

[63] Continuation of Ser. No. 108,126, Aug. 17, 1993, abandoned, which is a continuation-in-part of Ser. No. 591,104, Sep. 28, 1990, Pat. No. 5,252,721.

[51] Int. Cl.⁶ .................. C07F 13/00; C07D 473/00; C07K 14/77
[52] U.S. Cl. .................. 534/10; 534/14; 548/303.7; 300/367; 300/404; 424/1.57; 424/1.65; 424/1.53
[58] Field of Search .................. 548/303.7; 534/10, 534/14; 530/391.3, 391.5, 391.7, 402, 403, 367, 404; 424/1.69, 1.73

[56] References Cited

U.S. PATENT DOCUMENTS

| | | | |
|---|---|---|---|
| 2,810,753 | 10/1957 | Bersworth | 260/534 |
| 4,571,430 | 2/1986 | Byrne et al. | 560/148 |
| 4,775,745 | 10/1988 | Ford et al. | 534/560 |
| 4,789,736 | 12/1988 | Canning et al. | 534/14 |
| 4,833,251 | 5/1989 | Musso et al. | 548/303 |
| 4,849,511 | 7/1989 | Verbruggen | 534/14 |
| 4,861,869 | 8/1989 | Nicolotti et al. | 530/402 |
| 4,863,713 | 9/1989 | Goodwin et al. | 424/1.1 |
| 4,883,862 | 11/1989 | Chervu et al. | 530/331 |
| 4,895,955 | 1/1990 | Ford et al. | 548/303 |
| 4,897,255 | 1/1990 | Fritzberg et al. | 424/1.1 |
| 4,898,951 | 2/1990 | Symons | 548/303 |
| 4,963,682 | 10/1990 | Bodor | 546/338 |
| 4,963,688 | 10/1990 | Bodor | 546/316 |
| 4,965,392 | 10/1990 | Fritzberg et al. | 558/254 |
| 4,988,496 | 1/1991 | Srinivasan et al. | 424/1.1 |
| 5,256,395 | 10/1993 | Barbet et al. | 424/9 |
| 5,283,342 | 2/1994 | Gustavson et al. | 548/304.1 |

OTHER PUBLICATIONS

Lever et al., *Tetrahedron Letters*, vol. 29, No. 26, pp. 3219–3222, 1988 (Printed in Great Britain), "Synthesis of a novel bifunctional chelate designed for labeling proteins with technetium–99m".

Mastrostamatis et al., *Eur. J. Nucl. Med.*, Suppl. to vol. 16, 1990, Abstract No. 428, "Tripodal N,S₃–donor ligands as a new backbone for reduced technetium".

Corbin et al., *Inorganica Chimica Acta*, 90 (1984), pp. 41–51, "Preparation and properties of tripodal and linear tetradentate N,S–donor ligands and their complexes containing the $MoO_2^{2+}$ core".

Green, "The use of [¹⁴C]Biotin for Kinetic Studies and for Assay", *Biochem. J.*, vol. 89, p. 585, 1963.

Kalofonos et al., "Imaging of Tumor in Patients with Indium–111–Labeled Biotin and Streptavidin–Conjugated Antibodies: Preliminary Communication," *J. Nucl. Med.*, vol. 31, No. 11, pp. 1791–1796, 1990.

Hnatowich et al., "Investigations of Avidin and Biotin for Imaging Applications," *J. Nucl. Med.*, vol. 28, No. 8, pp. 1294–1302, 1987.

Paganelli et al., "Intraperitoneal Radio–Localization of Tumors Pre–targeted by Biotinylated Monoclonal Antibodies," *Int. J. Cancer*, vol. 45, pp. 1184–1189, 1990.

Paganelli et al., "Monoclonal antibody pretargeting techniques for tumour localization: the avidin–biotin system," *Nucl. Med. Communications*, vol. 12, pp. 211–234, 1991.

Goodwin/Hnatowich, Letter to the Editor/Reply, *J. Nucl. Med.*, vol. 32, No. 4 pp. 750–751, 1991.

Rosebrough, Abstract No. 235, *J. Nucl. Med.*, p. 880, 1992, "Plasma stability and Pharmacokinetics of Radio–labeled Deferozamine–Biotin Derivatives."

Virzi et al., Abstract No. 403, *J. Nucl. Med.*, p. 920, 1992, "The preparation and Evaluation of 12 Biotin Derivatives labeled with Tc–99m."

Rosario et al., Abstract No. 356, *J. Nucl. Med.*, vol. 32, No. 5, p. 993, 1991, "Bolton–Hunter and Biotin derivatized polylysine: A new multi–valent peptide reagent for *in vivo* pre–targeting with streptavidin conjugates."

*Primary Examiner*—Shean C. Wu
*Assistant Examiner*—Lara E. Chapman
*Attorney, Agent, or Firm*—Burns, Doane, Swecker & Mathis

[57] ABSTRACT

Novel chelating compounds and the corresponding radionuclide metal chelates are useful for radiolabeling proteins such as antibodies, ligands such as biotin and anti-ligands such as streptavidin with radionuclide metals such as ⁹⁹ᵐTc, ¹⁸⁶Re, and ¹⁸⁸Re. The radiolabeled proteins, ligands and anti-ligands have diagnostic or therapeutic use, depending on the radionuclide metal chosen.

17 Claims, 1 Drawing Sheet

S₃N CHELATING COMPOUNDS FOR THE RADIOLABELING OF LIGANDS, ANTI-LIGANDS OR OTHER PROTEINS

CROSS REFERENCE TO RELATED APPLICATIONS

This application is a continuation of application Ser. No. 08/108,126, filed Aug. 17, 1993, now abandoned, which is a continuation-in-part application of U.S. Ser. No. 07/591,104, filed Sep. 28, 1990 now U.S. Pat. No. 5,252,721.

BACKGROUND

Radiolabeled proteins such as antibodies are used in a variety of diagnostic and therapeutic medical procedures. The increased specificity of monoclonal antibodies, compared to polyclonal antibodies, makes them even more useful for delivering diagnostic or therapeutic agents such as radioisotopes to desired target sites in vivo. A monoclonal antibody specific for a desired type of target cells such as tumor cells may be used to deliver a therapeutic radionuclide attached to the antibody to the target cells, thereby causing the eradication of the undesired target cells. Alternatively, a monoclonal antibody having a diagnostically effective radionuclide attached thereto may be administered, whereupon the radiolabeled antibody localizes on the target tissue. Conventional diagnostic procedures then may be used to detect the presence of the target sites within the patient. In contrast to such "chelate-labeled antibody" proceures, pretargeting approaches may be used to achieve therapeutic or diagnostic goals, which pretargeting approaches involve the interaction of two members of a high affinity binding pair such as a ligand-anti-ligand binding pair.

One method for radiolabeling proteins such as antibodies as well as proteinaceous and non-proteinaceous binding pair members involves attachment of radionuclide metal chelates to the proteins or binding pair members. Chelates having a variety of chemical structures have been developed for this purpose. The usefulness of such chelates is dependent upon a number of factors such as the stability of radionuclide binding within the chelate and the reactivity of the chelating compound with the desired protein or binding pair member. The efficiency of radiolabeling of the chelating compound to produce the desired radionuclide metal chelate also is important. Another consideration is the biodistribution of the radiolabeled protein or binding pair member and catabolites thereof in vivo. Localization in non-target tissues limits the total dosage of a therapeutic radiolabeled protein or binding pair member that can be administered, thereby decreasing the therapeutic effect. In diagnostic procedures, localization in non-target tissues may cause undesirable background and/or result in misdiagnosis. The need remains for improvement in these and other characteristics of radionuclide metal chelate compounds used for radiolabeling of proteins such as antibodies. The use of pretargeting approaches diminishes non-target tissue localization of radiolabel; however, the need remains for improvement in molecules incorporating chelates and binding pair members of proteinaceous or non-proteinaceous structure.

SUMMARY OF THE INVENTION

The present invention provides chelating compounds useful as protein or binding pair member labeling reagents, the corresponding radionuclide metal chelates, and targeting molecules such as proteins or binding pair members radiolabeled therewith. The radiolabeled proteins or binding pair members of the present invention have use in various assays as well as in vivo diagnostic and therapeutic procedures. The protein may be a monoclonal antibody that binds to cancer cells, for example. The binding pair member may be a ligand or an anti-ligand, for example.

The chelating compounds or chelate-binding pair member conjugates of the present invention include compounds of the formulas:

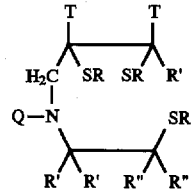

(I)

and

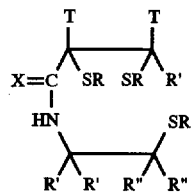

(II)

wherein:
each R is a protecting group;
Q is hydrogen or a protecting group;
each T is independently chosen from hydrogen, lower alkyl groups of from 1 to about 6 carbon atoms, electron withdrawing groups, and lower alkyl groups of from 1 to about 6 carbon atoms substituted with electron withdrawing group(s);
X represents O, S, or NH;
each R' is independently selected from:
—(CH₂)ₙ—COOH with n=0 to about 4,
—(CH₂)ₙ—Z, wherein Z represents a conjugation group reactive with a protein, a ligand or an anti-ligand; a ligand; or an anti-ligand; a ligand-linker moiety or an anti-ligand linker moiety wherein the linker moiety is a portion of a ligand or an anti-ligand conjugation group and wherein n=0 to about 4,
hydrogen, and
a lower alkyl group of from 1 to about 6 carbon atoms;
each R" is independently selected from:
—(CH₂)ₙ—COOH, with n=0 to about 4,
hydrogen, and
a lower alkyl group of from 1 to about 6 carbon atoms; and
the compound comprises at least one —(CH₂)ₙ—Z substituent. The conjugation group Z serves to react with a protein or binding pair member to bind the chelating compound thereto. Alternatively, Z may itself constitute or include a binding pair member.

The compounds of formulas I and II are reacted with molecules such as proteins or binding pair members to attach the compounds to the proteins or binding pair members. The compounds may be radiolabeled before or after attachment to the protein or binding pair member. The resulting radiolabeled proteins or binding pair members have diagnostic or therapeutic use, depending on the particular radionuclide employed.

The nitrogen atom and three sulfur atoms shown in formulas (I) and (II) are believed to function as donor atoms that are bonded to the radionuclide metal in the corresponding chelate. The compounds of formulas (I) and (II) thus may be designated S₃N chelating compounds.

Radiolabeling of the chelating compounds of formulas I and II produces the radionuclide metal chelates of formulas III and IV, respectively:

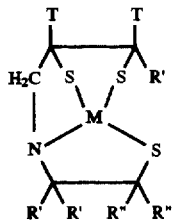

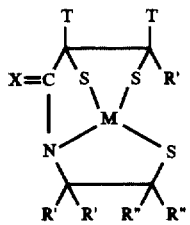

wherein M represents a radionuclide metal or oxide thereof and the other symbols are as defined above. Preferred radionuclide metals include $^{99m}$Tc, $^{188}$Re, and $^{186}$Re.

The present invention also provides protein-chelating compound conjugates resulting from reaction of a Z group of compounds I or II with a protein. In addition, ligand- or anti-ligand-chelating compound conjugates resulting from reaction of an appropriate Z conjugation group of certain embodiments of the present invention with a ligand or anti-ligand are contemplated as additional embodiments of the present invention. Radiolabeled proteins, ligands or anti-ligands comprising a radionuclide metal chelate of formula III or IV attached to a targeting protein, ligand or anti-ligand also are provided by the present invention. An example of a ligand is biotin, with the complementary anti-ligand thereof being avidin or streptavidin, wherein biotin and avidin or streptavidin together form a ligand-anti-ligand binding pair.

DETAILED DESCRIPTION OF THE INVENTION

Figure 1:
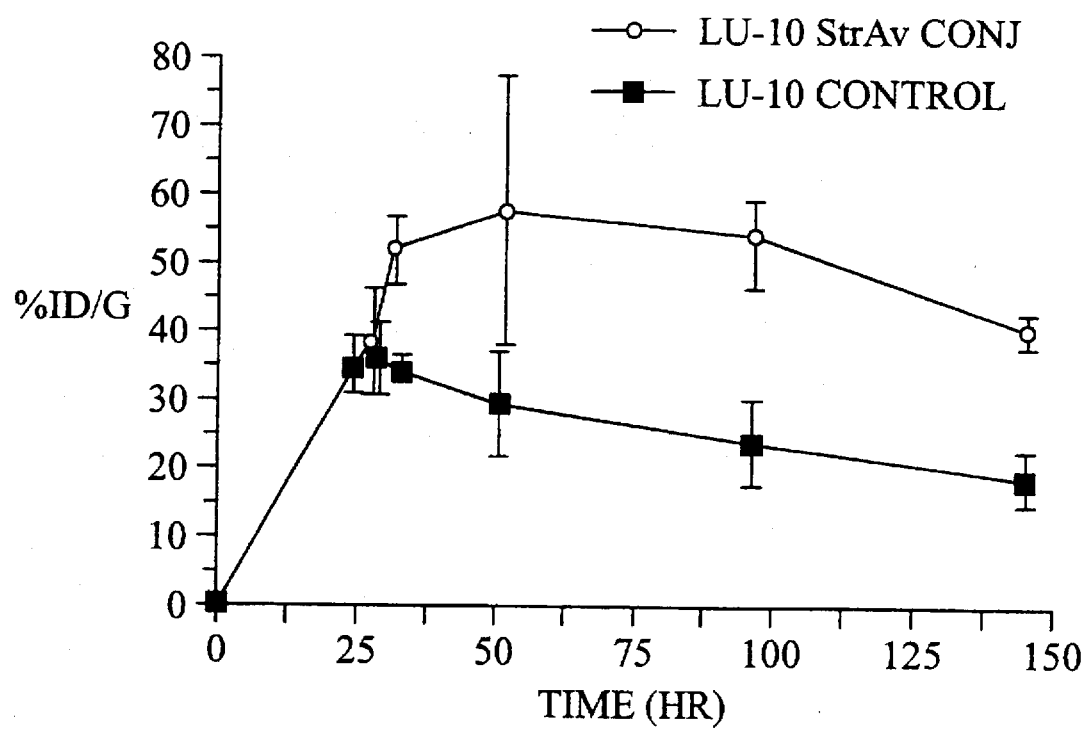
FIG. 1 depicts the tumor uptake profile of NR-LU-10-streptavidin conjugate (Lu-10-StrAv) in comparison to a control profile of nature NR-LU-10 whole antibody.

Prior to setting forth the invention, it may be helpful to set forth definitions of certain terms to be used within the disclosure.

Targeting moiety or Targeting molecule: A molecule that binds to a defined population of cells. The targeting moiety may bind a receptor, an oligonucleotide, an enzymatic substrate, an antigenic determinant, or other binding site present on or in the target cell population. Targeting moieties that are proteins are referred to herein as "targeting proteins." Antibody is used throughout the specification as a prototypical example of a targeting moiety and a targeting protein. Tumor is used as a prototypical example of a target in describing the present invention.

Ligand/anti-ligand pair: A complementary/anti-complementary set of molecules that demonstrate specific binding, generally of relatively high affinity. Exemplary ligand/anti-ligand pairs include zinc finger protein/dsDNA fragment, hapten/antibody, lectin/carbohydrate, ligand/receptor, and biotin/avidin. Biotin/avidin is used throughout the specification as a prototypical example of a ligand/anti-ligand pair.

Anti-ligand: As defined herein, an "anti-ligand" demonstrates high affinity, and preferably, multivalent binding of the complementary ligand. Preferably, the anti-ligand is large enough to avoid rapid renal clearance, and contains sufficient multivalency to accomplish crosslinking and aggregation of targeting moiety-ligand conjugates. Univalent anti-ligands are also contemplated by the present invention. Anti-ligands of the present invention may exhibit or be derivitized to exhibit structural features that direct the uptake thereof, e.g., galactose residues that direct liver uptake. Avidin and streptavidin are used herein as prototypical anti-ligands.

Avidin and Streptavidin: As defined herein, both of the terms "avidin" and "streptavidin" include avidin, streptavidin and derivatives and analogs thereof that are capable of high affinity, multivalent or univalent binding of biotin.

Ligand: As defined herein, a "ligand" is a relatively small, soluble molecule that exhibits rapid serum, blood and/or whole body clearance when administered intravenously in an animal or human. Biotin is used as the prototypical ligand.

Pretargeting: As defined herein, pretargeting involves target site localization of a targeting moiety that is conjugated with one member of a ligand/anti-ligand pair; after a time period sufficient for optimal target-to-non-target accumulation of this targeting moiety conjugate, active agent conjugated to the opposite member of the ligand/anti-ligand pair is administered and is bound (directly or indirectly) to the targeting moiety conjugate at the target site (two-step pretargeting). Three-step and other related methods described herein are also encompassed.

Linker Moiety: A moiety that is a portion of a protein, ligand or anti-ligand conjugation group that remains part of the structure of a protein-chelate, ligand-chelate or anti-ligand-chelate conjugate following the conjugation step. For example, the linker moiety of an active ester chelate derivative includes, for example, a carbonyl (—CO—) moiety.

The present invention provides chelating compounds useful as protein or binding pair member labeling reagents, methods for radiolabeling proteins or binding pair members using these reagents, and the resulting radiolabeled proteins or binding pair members having use in diagnostic or therapeutic procedures. The protein or binding pair member labeling reagents and chelate-binding pair conjugates are of the following formulas I and II:

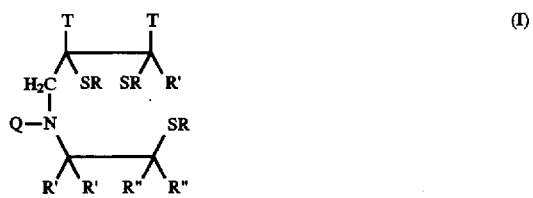

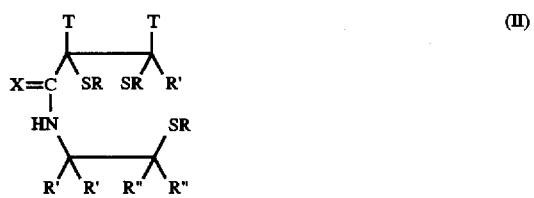

wherein:

each R is a protecting group;

Q is hydrogen or a protecting group;

each T is independently chosen from hydrogen, lower alkyl groups of from 1 to about 6 carbon atoms, electron withdrawing groups (e.g., nitro, sulfonate, or carboxylic acid groups), and lower alkyl groups of from 1 to about 6 carbon atoms substituted with electron withdrawing group(s);

X represents O, S, or NH;

each R' is independently selected from:
—$(CH_2)_n$—COOH with n=0 to about 4,
—$(CH_2)_n$—Z, wherein Z represents a conjugation group reactive with a protein, a ligand or an anti-ligand; a ligand; or an anti-ligand; or a ligand-linker moiety or an anti-ligand-linker moiety wherein the linker moiety is a portion of a ligand or an anti-ligand conjugation group and wherein n=0 to about 4, hydrogen, and
a lower alkyl group of from 1 to about 6 carbon atoms (preferably 1 or 2 carbon atoms);

each R" is independently selected from:
—$(CH_2)_n$—COOH, with n=0 to about 4, hydrogen, and
a lower alkyl group of from 1 to about 6 carbon atoms (preferably 1 or 2 carbon atoms); and the compound comprises at least one —$(CH_2)_n$—Z substituent.

For the reagents of formulas (I) and (II), the two T substituents preferably are identical (preferably, both are methyl groups, most preferably, both are hydrogen).

Further, the compounds preferably comprise only one —$(CH_2)_n$—COOH substituent and only one —$(CH_2)_n$—Z substituent. The —$(CH_2)_n$—COOH substituent generally increases the water solubility of the compound.

The conjugation group Z is a functional group that will react with a functional group on a molecule to be radiolabeled (e.g., a targeting protein, a ligand or an anti-ligand) thereby attaching the chelating compound thereto. Radiolabeling of the chelating compound produces a radionuclide metal chelate attached to the targeting protein, ligand or anti-ligand. The chelating compounds of the present invention each comprise at least one conjugation group, as described in more detail below.

In the compound of formula I, Q represents hydrogen or any suitable nitrogen protecting group (a number of which are known) such as an alkyl group of 1 to 6 carbon atoms. Q preferably is hydrogen or a methyl group.

For the compounds of formula II, X preferably is O.

R represents any suitable sulfur protecting group. A number of protecting groups, including but not limited to acyl, aryl, and alkyl groups, are known for use in protecting sulfur atoms. The protecting groups should be removable, either prior to or during the radiolabeling reaction. The protecting groups on the three sulfur atoms may be the same or different. In some cases, a single protecting group (e.g., a thioacetal) may serve to protect two sulfur atoms, as shown below.

Among the suitable sulfur protecting groups are hemithioacetal, thioacetal, benzyl, and acetamidomethyl protecting groups. Also useful are acyl type groups such as those of the formula

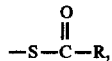

wherein the S is a sulfur atom of the chelating compound and R is an alkyl or aryl group. Examples are isobutyryl, benzoyl, and acetyl protecting groups.

When hemithioacetal protective groups are used, each sulfur atom to be protected has a separate protective group attached to it, which together with the sulfur atom defines a hemithioacetal group. The hemithioacetal groups contain a carbon atom bonded directly (i.e., without any intervening atoms) to a sulfur atom and an oxygen atom, i.e.,

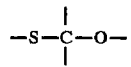

Preferred hemithioacetals generally are of the following formula, wherein the sulfur atom is a sulfur atom of the chelating compound:

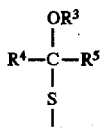

wherein $R^3$ is a lower alkyl group, preferably of from two to five carbon atoms, and $R^4$ is a lower alkyl group, preferably of from one to three carbon atoms. Alternatively, $R^3$ and $R^4$ may be taken together with the carbon atom and the oxygen atom shown in the formula to define a nonaromatic ring, preferably comprising from three to seven carbon atoms in addition to the carbon and oxygen atoms shown in the formula. $R^5$ represents hydrogen or a lower alkyl group wherein the alkyl group preferably is of from one to three carbon atoms. Examples of such preferred hemithioacetals include, but are not limited to:

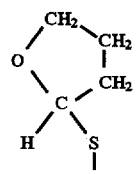 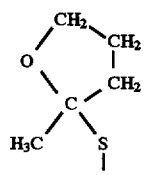

Tetrahydrofuranyl      2-methyl tetrahydrofuranyl

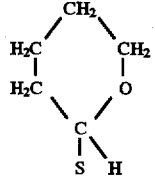 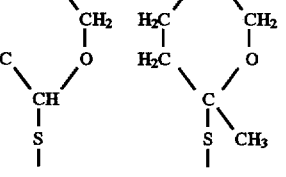

Tetrahydropyranyl    ethoxyethyl    2-methyl tetrahydropyranyl

Other hemithioacetal sulfur protecting groups include those derived from monosaccharides, such as the following, wherein the sulfur atom is a sulfur donor atom of the chelating compound:

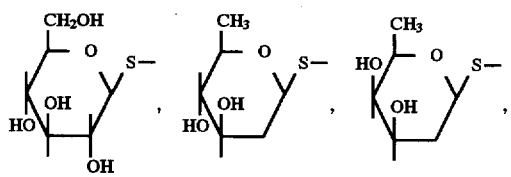

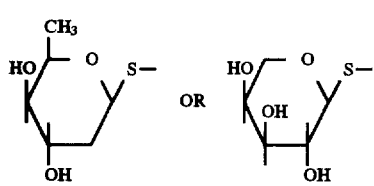

Examples of thioacetal protecting groups are as follows, wherein two sulfur atoms (the two sulfur atoms attached to adjacent carbon atoms in the chelating compound) are attached to a single protecting group:

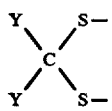

wherein each Y is independently selected from hydrogen, alkyl groups of 1 to 6 carbons (preferably methyl or ethyl), alkoxy groups of 1 to 6 carbons (preferably 1 or 2 carbon atoms), phenyl groups, and phenyl rings having an electron donating group (e.g., hydroxy, methoxy, or ethoxy group) bonded directly thereto. The two sulfur atoms shown are sulfur donor atoms of the chelating compound which, together with the protecting group, form the thioacetal group. Suitable thioacetals include, but are not limited to, the following:

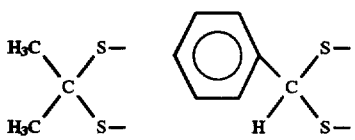

Representative examples of the compounds of formula (I) include, but are not limited to:

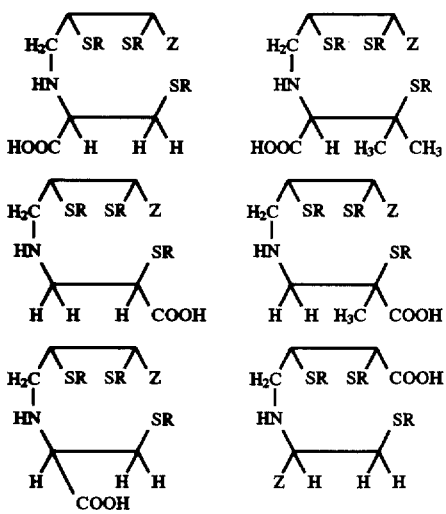

Representative examples of the compounds of formula (II) include but are not limited to:

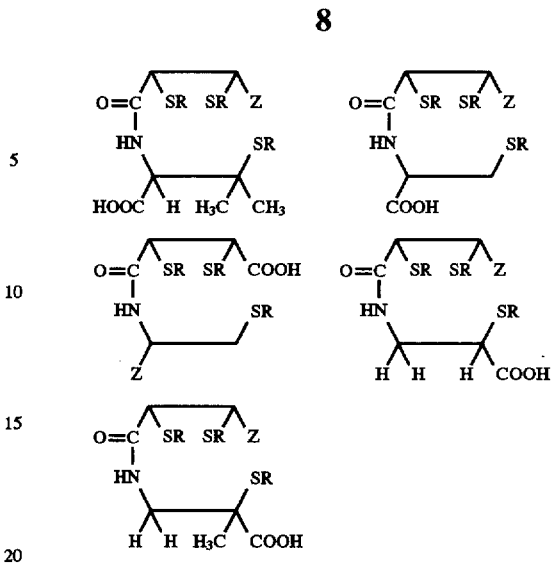

In preferred chelating compounds of the present invention, Z represents an active ester (described below). The two sulfur atoms that are attached to immediately adjacent carbon atoms (i.e., the vicinal dithiol portion of the compound) preferably are attached to a single protecting group (e.g., a thioacetal). The remaining sulfur atom preferably is protected by a different group such as a benzyl group.

The compounds of formulas I and II are useful as reagents for radiolabeling other molecules. The chelating compounds may be attached to the molecule to be radiolabeled either before or after the radiolabeling reaction. The molecule should contain (or be modified to contain) a functional group such as a primary amine or sulfhydryl that will react with the conjugation group on the chelating compound. The molecule may be any such molecule to be radiolabeled for use in in vitro assays, diagnostic or therapeutic procedures in vivo, or other such purpose.

In one embodiment of the invention, the molecule to be radiolabeled is a targeting molecule. The targeting molecule is any molecule that will serve to deliver the radionuclide metal chelate to a desired target site (e.g., target cells) in vitro or in vivo. Examples of targeting molecules include, but are not limited to, steroids, lymphokines, and those drugs and proteins that bind to a desired target site.

The "targeting moiety" of the present invention binds to a defined target cell population, such as tumor cells. Preferred targeting moieties useful in this regard include antibody and antibody fragments, proteinaceous and non-proteinaceous ligands or anti-ligands, peptides, and hormones. Proteins corresponding to or binding to known cell surface receptors (including low density lipoproteins, transferrin and insulin), fibrinolytic enzymes, anti-HER2, platelet binding proteins such as annexins, and biological response modifiers (including interleukin, interferon, erythropoietin and colony-stimulating factor) are also preferred targeting moieties. Also, anti-EGF receptor antibodies, which internalize following binding to the EGF receptor and which traffic to the nucleus, are preferred targeting moieties for use in the present invention to facilitate delivery of Auger emitters and nucleus binding drugs to target cell nuclei. Oligonucleotides, e.g., antisense oligonucleotides that are complementary to portions of target cell nucleic acids (DNA or RNA), are also useful as targeting moieties in the practice of the present invention. Oligonucleotides binding to cell surfaces are also useful. Analogs of the above-listed targeting moieties that retain the capacity to bind to a defined target cell population may also be used within the claimed invention. In addition, synthetic targeting moieties may be designed.

Functional equivalents of the aforementioned molecules are also useful as targeting moieties of the present invention. One targeting moiety functional equivalent is a "mimetic" compound, an organic chemical construct designed to mimic a proper configuration and/or orientation for targeting moiety-target cell binding. Another targeting moiety functional equivalent is a short polypeptide designated as a "minimal" polypeptide, constructed using computer-assisted molecular modeling and mutants having altered binding affinity, which minimal polypeptides exhibit the binding affinity of the targeting moiety.

The targeting molecule may be a targeting protein, which is capable of binding to a desired target site. The term "protein" as used herein includes proteins, polypeptides, and fragments thereof, including proteinaceous ligands and anti-ligands. The targeting protein may bind to a receptor, substrate, antigenic determinant, complementary binding pair member or other binding site on a target cell or other target site. The targeting protein serves to deliver the radionuclide attached thereto to a desired target site in vivo. Examples of targeting proteins include, but are not limited to, antibodies and antibody fragments, proteinaceous ligands or anti-ligands, hormones, fibrinolytic enzymes, and biologic response modifiers. In addition, other polymeric molecules that localize in a desired target site in vivo, although not strictly proteins, are included within the definition of the term "targeting proteins" as used herein. For example, certain carbohydrates or glycoproteins may be used in the present invention. The proteins may be modified, e.g., to produce variants and fragments thereof, as long as the desired biological property (i.e., the ability to localize at the target site) is retained. The proteins may be modified by using various genetic engineering or protein engineering techniques, for example.

Among the preferred targeting proteins are antibodies, most preferably monoclonal antibodies. A number of monoclonal antibodies that bind to a specific type of cell have been developed, including monoclonal antibodies specific for tumor-associated antigens in humans. Among the many such monoclonal antibodies that may be used are anti-TAC, or other interleukin-2 receptor antibodies; 9.2.27 and NR-ML-05, reactive with the 250 kilodalton human melanoma-associated proteoglycan; and NR-LU-10, reactive with a pancarcinoma glycoprotein. The antibody employed in the present invention may be an intact (whole) molecule, a fragment thereof, or a functional equivalent thereof. Examples of antibody fragments are F(ab')$_2$, Fab', Fab, and F$_v$ fragments, which may be produced by conventional methods or by genetic or protein engineering.

Human monoclonal antibodies or "humanized" murine antibodies are also useful as targeting moieties in accordance with the present invention. For example, murine monoclonal antibody may be "humanized" by genetically recombining a nucleotide sequence encoding the murine Fv region (i.e., containing the antigen binding site which antibodies are also known as chimeric antibodies) or the complementarity determining regions thereof with a nucleotide sequence encoding at least a human constant domain region and an Fc region, e.g., in a manner similar to that disclosed in European Patent Application No. 0,411,893 A2. Some additional murine residues may also be retained within the human variable region framework domains to ensure proper target site binding characteristics. Humanized targeting moieties are recognized to decrease the immunore-activity of the antibody or polypeptide in the host recipient, permitting an increase in the half-life and a reduction in the possibility of adverse immune reactions.

Ligands suitable for use within the present invention include biotin, haptens, lectins, epitopes, dsDNA fragments and analogs and derivatives thereof. Useful complementary anti-ligands include avidin (for biotin), carbohydrates (for lectins), antibody, fragments or analogs thereof, including mimetics (for haptens and epitopes) and zinc finger proteins (for dsDNA fragments). Preferred ligands and anti-ligands bind to each other with an affinity of at least about $k_D \geq 10^9 M$.

The chelating compounds of the present invention comprise at least one (and preferably only one) conjugation group Z. A conjugation group is a chemically reactive functional group that will react with a molecule to be radiolabeled to bind the chelating compound thereto. When the targeting molecule is a protein, the conjugation group is reactive under conditions that do not denature or otherwise adversely affect the protein. Examples of suitable conjugation groups include but are not limited to active esters, isothiocyanates, amines, hydrazines, maleimides or other Michael-type acceptors, thiols, and activated halides. Among the preferred active esters are N-hydroxysuccinimidyl ester, sulfosuccinimidyl ester, thiophenyl ester, 2,3,5,6-tetrafluorophenyl ester, and 2,3,5,6-tetrafluorothiophenyl ester. The latter three preferred active esters may comprise a group that enhances water solubility, at the para (i.e., 4) or the ortho position on the phenyl ring. Examples of such groups are $CO_2H$, $SO_3^-$, $PO_3^{2-}$, $OPO_3^{2-}$, $OSO_3^-$, $N^+R_3$ wherein each R represents H or an alkyl group, and $O(CH_2CH_2O)_nCH_3$ groups.

A ligand or anti-ligand conjugation group (i.e., a group located on a chelate compound that is reactive with a ligand or an anti-ligand) is a chemically reactive functional group that will react with a ligand or anti-ligand under conditions that do not adversely affect the ligand or anti-ligand, including the capacity of the ligand or anti-ligand to bind to its complementary binding pair member. Ligand or anti-ligand conjugation groups therefore are sufficiently reactive with a functional group on a ligand or anti-ligand so that the reaction can be conducted under relatively mild reaction conditions including those described above for protein-chelate conjugation. For proteinaceous ligands or anti-ligands, such as streptavidin, protein conjugation groups may correspond to ligand or anti-ligand conjugation groups. Examples of suitable ligand or anti-ligand conjugation groups therefore include, but are not limited to, active esters, isothiocyanates, amines, hydrazines, thiols, and maleimides. Among the preferred active esters are thiophenyl ester, 2,3,5,6-tetrafluorophenyl ester, and 2,3,5,6-tetrafluorothiophenyl ester. The preferred active esters may comprise a group that enhances water solubility, at the para (i.e., 4) position on the phenyl ring. Examples of such groups are $CO_2H$, $SO_3^-$, $PO_3^{2-}$, $OPO_3^{2-}$, and $O(CH_2CH_2O)_nCH_3$ groups.

For non-proteinaceous ligand or anti-ligand moieties, such as biotin, suitable conjugation groups are those functional groups that react with a ligand or anti-ligand functional group (e.g., a terminal carboxy group) or a functional group which the ligand or anti-ligand has been derivatized to contain (e.g., an alcohol or an amine group produced by the reduction of a terminal carboxy moiety). As a result, conjugation groups, such as those recited above, that are capable of reacting with —COOH, —OH or —NH$_2$ groups are useful conjugation groups for producing biotin conjugates of this aspect of the present invention. Exemplary biotin- COOH conjugation groups are amines, hydrazines, alcohols and the like. Exemplary biotin-OH conjugation groups are tosylates (Ts), active esters, halides and the like, with exemplary groups being reactive with biotin-O-Ts including amines, hydrazines, thiols and the like. Exemplary biotin-$NH_2$ conjugation groups are active esters, acyl chlorides, tosylates, isothiocyanates and the like.

Proteins contain a variety of functional groups; e.g., carboxylic acid (COOH) or free amine (—$NH_2$) groups, which are available for reaction with a suitable conjugation group on a chelating compound to bind the chelating compound to the protein. For example, an active ester on the chelating compound reacts with epsilon amine groups on lysine residues of proteins to form amide bonds. Alternatively, a targeting molecule and/or a chelator may be derivatized to expose or attach additional reactive functional groups. The derivatization may involve attachment of any of a number of linker molecules such as those available from Pierce Chemical Company, Rockford, Ill. Alternatively, the derivatization may involve chemical treatment of the protein (which may be an antibody). Procedures for generation of free sulfhydryl groups on antibodies or antibody fragments by reducing disulfide bonds are also known. Maleimide conjugation groups on a chelating compound are reactive with the sulfhydryl (thiol) groups.

Alternatively, when the targeting molecule, ligand or anti-ligand is a carbohydrate or glycoprotein, derivatization may involve chemical treatment of the carbohydrate; e.g., glycol cleavage of the sugar moiety of a glycoprotein antibody with periodate to generate free aldehyde groups. The free aldehyde groups on the antibody may be reacted with free amine or hydrazine conjugation groups on the chelator to bind the chelator thereto. (See U.S. Pat. No. 4,671,958.)

Biotin has a terminal carboxy moiety which may be reacted with a suitable ligand conjugation group, such as an amine, hydroxyl in the presence of a coupling agent such as DCC or the like. In addition, the terminal carboxy moiety may be derivatized to form an active ester, which is suitable for reaction with a suitable ligand conjugation group, such as an amine, a hydroxyl, another nucleophile, or the like. Alternatively, the terminal carboxy moiety may be reduced to a hydroxy moiety for reaction with a suitable ligand conjugation group, such as a halide (e.g., iodide, bromide or chloride), tosylate, mesylate, other good leaving groups or the like. The hydroxy moiety may be chemically modified to form an amine moiety, which may be reacted with a suitable ligand conjugation group, such as an active ester or the like.

The chelating compounds of the present invention are radiolabeled, using conventional procedures, with any of a variety of radionuclide metals to form the corresponding radionuclide metal chelates. The radiolabeling may be conducted before or after the chelating compound is attached to the molecule to be radiolabeled. These radionuclide metals include, but are not limited to, copper (e.g., $^{67}Cu$ and $^{64}Cu$); technetium (e.g., $^{99m}Tc$); rhenium (e.g., $^{186}Re$ and $^{188}Re$); lead (e.g., $^{212}Pb$); bismuth (e.g., $^{212}Bi$); palladium (e.g., $^{109}Pd$); and rhodium (e.g., $^{105}Rh$). Methods for preparing these isotopes are known. Molybdenum/technetium generators for producing $^{99m}Tc$ are commercially available. Procedures for processing $^{186}Re$ include the procedures described by Deutsch et al., (Nucl. Med. Biol. Vol. 13:4:465–477, 1986) and Vanderheyden et al. (Inorganic Chemistry, Vol. 24:1666–1673, 1985), and methods for production of $^{188}Re$ have been described by Blachot et al. (Int. J. Applied Radiation and Isotopes Vol. 20:467–470, 1969) and by Klofutar et al. (J. of Radioanalytical Chem., Vol. 5:3–10, 1970). Production of $^{109}Pd$ is described in Fawwaz et al., J. Nucl. Med. (1984), 25:796. Production of $^{212}Pb$ and $^{212}Bi$ is described in Gansow et al., Amer. Chem. Soc. Symp. Ser. (1984), 241:215–217, and Kozah et al., Proc. Nat'l. Acad. Sci. U.S.A. (January 1986) 83:474–478. $^{99m}Tc$ is preferred for diagnostic use, and the other radionuclides listed above have therapeutic use.

The radionuclide advantageously is in chelatable form when reacted with the chelating compounds of the invention. In the case of technetium and rhenium, being in "chelatable form" generally requires a reducing step. A reducing agent will be employed to reduce the radionuclides (e.g., in the form of pertechnetate and perrhenate, respectively) to a lower oxidation state at which chelation will occur. Many suitable reducing agents, and the use thereof, are known. (See, for example, U.S. Pat. Nos. 4,440,738; 4,434,151; and 4,652,440.) Such reducing agents include, but are not limited to, stannous ion (e.g., in the form of stannous salts such as stannous chloride or stannous fluoride), metallic tin, ferrous ion (e.g., in the form of ferrous salts such as ferrous chloride, ferrous sulfate, or ferrous ascorbate) and many others. Sodium pertechnetate (i.e., $^{99m}TcO_4^-$— which is in the +7 oxidation level) or sodium perrhenate (i.e., $^{188}ReO_4^-$—, $^{186}ReO_4^-$—) may be combined simultaneously with a reducing agent and a chelating compound of the invention in accordance with the radiolabeling method of the invention, to form a chelate.

Preferably, the radionuclide is treated with a reducing agent and a complexing agent to form an intermediate complex (i.e., an "exchange complex"). Complexing agents are compounds which bind the radionuclide more weakly than do the chelate compounds of the invention, and may be weak chelators. Any of the suitable known complexing agents may be used, including but not limited to gluconic acid, glucoheptonic acid, methylene hi- or di-phosphonate, glyceric acid, glycolic acid, tartaric acid, mannitol, oxalic acid, malonic acid, succinic acid, bicine, malic acid, N,N'-bis(2-hydroxy ethyl) ethylene diamine, citric acid, ascorbic acid and gentisic acid. Good results are obtained using gluconic acid or glucoheptonic acid as the technetium-complexing agent and citric acid for rhenium. When the radionuclide in the form of such an exchange complex is reacted with the chelating compounds of the invention (which may be attached to a targeting protein, ligand, anti-ligand or the like), the radionuclide will transfer to these chelating compounds which bind the radionuclide more strongly to form chelates of the invention. Radionuclides in the form of such exchange complexes also are considered to be in "chelatable form" for the purposes of the present invention.

Chelates of $^{212}Pb$, $^{212}Bi$, $^{103}Rh$, and $^{109}Pd$ may be prepared by combining the appropriate salt of the radionuclide with the chelating compound and incubating the reaction mixture at room temperature or at higher temperatures. It is not necessary to treat the lead, bismuth, rhodium, palladium, and copper radioisotopes with a reducing agent prior to chelation, as such isotopes are already in an oxidation state suitable for chelation (i.e., in chelatable form).

The specific radiolabeling reaction conditions may vary somewhat according to the particular radionuclide and chelating compound involved. When the chelating compound is attached to a targeting protein or a proteinaceous ligand or anti-ligand prior to radiolabeling, the radiolabeling reaction is conducted under physiologically acceptable conditions to avoid denaturing or otherwise damaging the protein.

The present invention also provides a method for radiolabeling targeting proteins by attaching a chelating compound of formula I or II to the protein, then reacting the resulting protein-chelating compound conjugate with a radionuclide metal in chelatable form. Alternatively, the chelating compound is first reacted with a radionuclide metal in chelatable form, and the resulting radionuclide metal chelate is reacted with the protein. In either case, a protein having a radionuclide metal chelate attached thereto is produced. Analogous methods of production of radiolabeled chelate-ligand and radiolabeled chelate-anti-ligand are also contemplated. Details of these reactions are presented in the examples below.

The invention thus provides ligand-, anti-ligand- and protein-chelating compound conjugates of formulas V and VI, produced by reacting a ligand, an anti-ligand or a protein with a chelating compound of formula I or II, respectively:

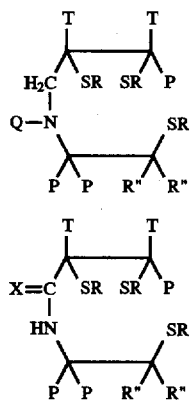

wherein:

one P represents a substituent —(CH$_2$)$_n$—P' with n=0 to about 4 and P' representing a ligand, an anti-ligand or a protein; and the remaining substituents P are independently selected from:
—(CH$_2$)$_n$—COOH with n=0 to about 4,
hydrogen, and
a lower alkyl group of from 1 to about 6 carbon atoms;
with the other symbols having the definition presented for formulas I and II above.

Also provided by the present invention are radiolabeled proteins of the following formulas:

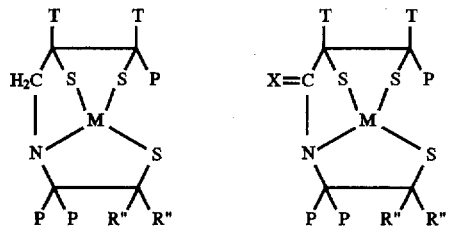

wherein:

M represents a radionuclide metal or oxide thereof;

one P represents a substituent —(CH$_2$)$_n$—P' with n=0 to about 4 and P' representing a ligand, an anti-ligand or a protein; and the remaining substituents P are independently selected from:
—(CH$_2$)$_n$—COOH with n=0 to about 4,
hydrogen, and
a lower alkyl group of from 1 to about 6 carbon atoms;

with the other symbols having the definition presented for formulas I and II above.

The protein P' may be a targeting protein as described above or a ligand or anti-ligand as described above. It is to be understood that the protein P' may include a portion of the conjugation group Z that reacted with the protein. Similarly, ligand or anti-ligand P' moieties may include a poration of the conjugation group Z that reacted with the ligand or anti-ligand.

The radiolabeled targeting proteins, ligands or anti-ligands of the present invention have use in diagnostic and therapeutic procedures, both for in vitro assays and for in vivo medical procedures. One type of therapeutic or diagnostic procedure in which the compounds of the present invention may be employed is a pretargeting protocol. Generally, pretargeting encompasses two protocols, termed the three-step and the two-step. In the three-step protocol, shown schematically below, targeting moiety-ligand is administered and permitted to localize to target.

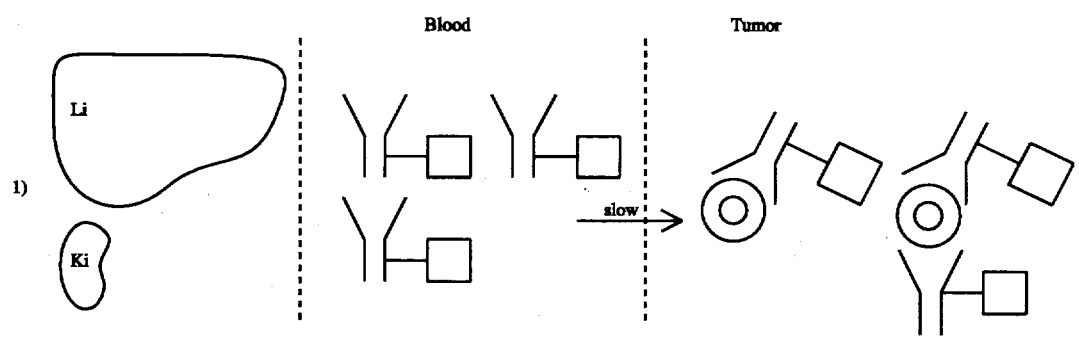

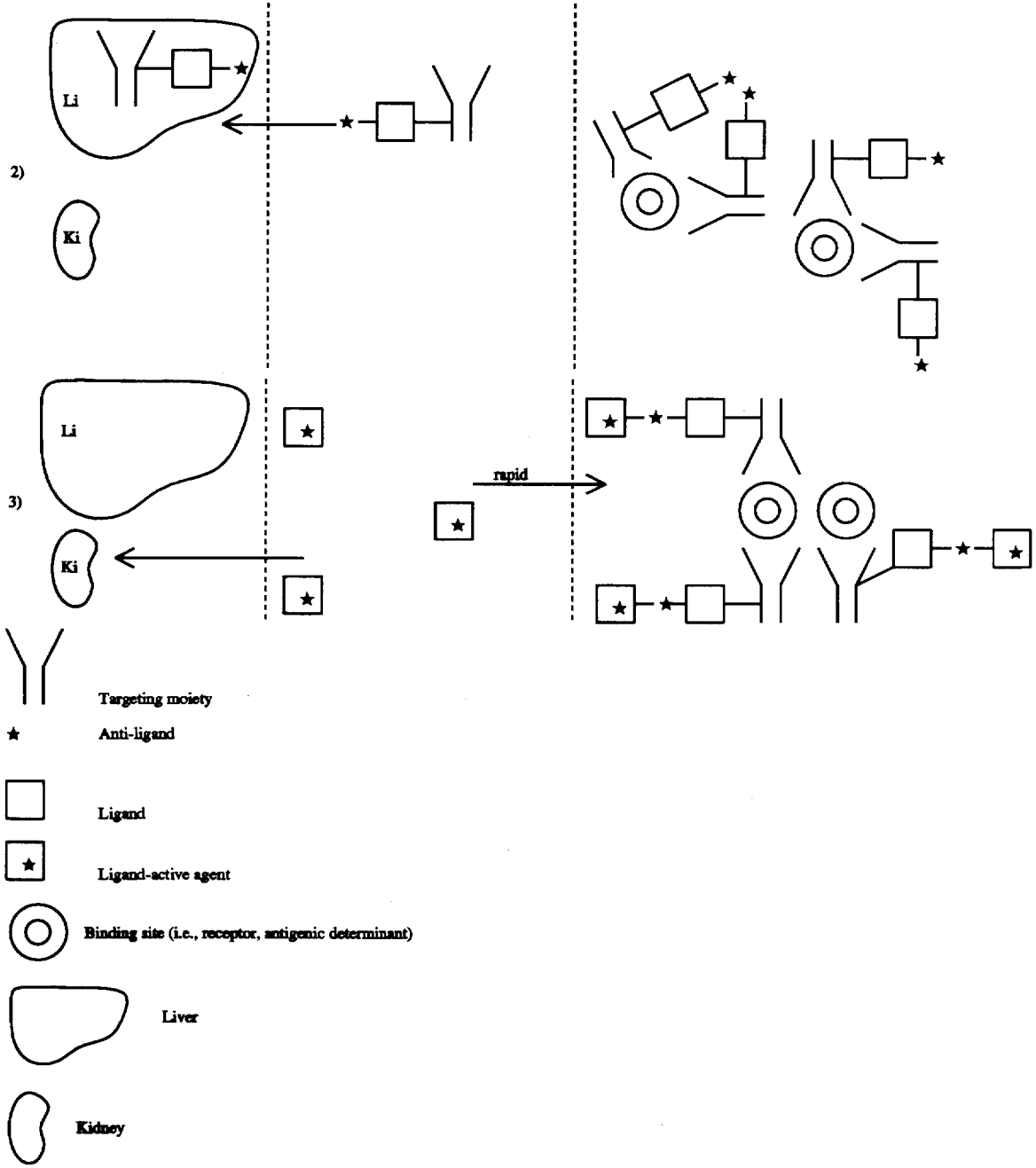

Targeting moiety-ligand conjugates may be prepared in accordance with known techniques therefor. Anti-ligand is then administered to act as a clearing agent and to facilitate and direct the excretion of circulating targeting moiety-ligand. The anti-ligand also binds to target-associated targeting moiety-ligand. Next, a conjugate employing a compound of the present invention is administered, having the following structure:

Ligand—Chelate—Radionuclide

The radiolabeled ligand conjugate either binds to target-associated targeting moiety-ligand-anti-ligand or is rapidly excreted, with the excretion proceeding primarily through the renal pathway. Consequently, the target-non-target ratio of active agent is improved, and undesirable hepatobiliary excretion and intestinal uptake of the active agent are substantially decreased.

Two-step pretargeting involves administration of targeting moiety-anti-ligand, which may be prepared in accordance with known techniques therefor. After permitting the administered agent to localize to target, a radiolabeled ligand of the present invention is administered. Preferably, as a "step 1.5," a clearing agent is administered to remove circulating targeting moiety-anti-ligand without binding of clearing agent to target-associated targeting moiety-anti-ligand. In this manner, the target-non-target ratio of the radiolabeled ligand is increased, and undesirable hepatobiliary excretion and intestinal uptake of the radiolabeled ligand are substantially decreased.

The radiolabeled molecules may be administered intravenously, intraperitoneally, intralymphatically, locally, or by other suitable means, depending on such factors as the type of target site. The amount to be administered will vary according to such factors as the type of radionuclide (e.g., whether it is a diagnostic or therapeutic radionuclide), the route of administration, the type of target site(s), the affinity of the targeting protein for the target site of interest, the affinity of the ligand and anti-ligand for each other and any cross-reactivity of the targeting protein ligand or anti-ligand with normal tissues. Appropriate dosages may be established by conventional procedures and a physician skilled in the field to which this invention pertains will be able to determine a suitable dosage for a patient. A diagnostically effective dose is generally from about 5 to about 35 and typically from about 10 to about 30 mCi per 70 kg body weight. A therapeutically effective dose is generally from about 20 mCi to about 300 mCi, depending on the radionuclide. Autologous bone marrow rescue may be required at the higher dose levels. Higher doses, e.g., ranging to an order of magnitude or more, may be administered using pretargeting procedures employed, because of the decoupling of targeting moiety localization and radionuclide localization, which decoupling results in a reduction in whole body absorbed dose. For diagnosis, conventional non-invasive procedures (e.g., gamma cameras) are used to detect the biodistribution of the diagnostic radionuclide, thereby determining the presence or absence of the target sites of interest (e.g., tumors).

The following examples are presented to illustrate certain embodiments of the invention, and are not to be construed as limiting the scope of the present invention.

EXAMPLE I

Synthesis of a Chelating Compound

The synthesis procedure is generally depicted in the following reaction scheme:

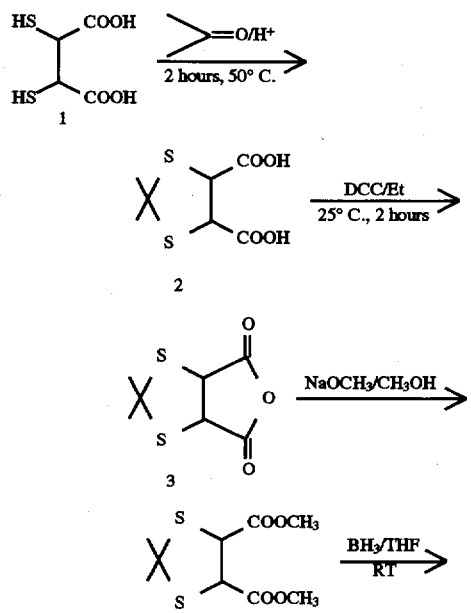

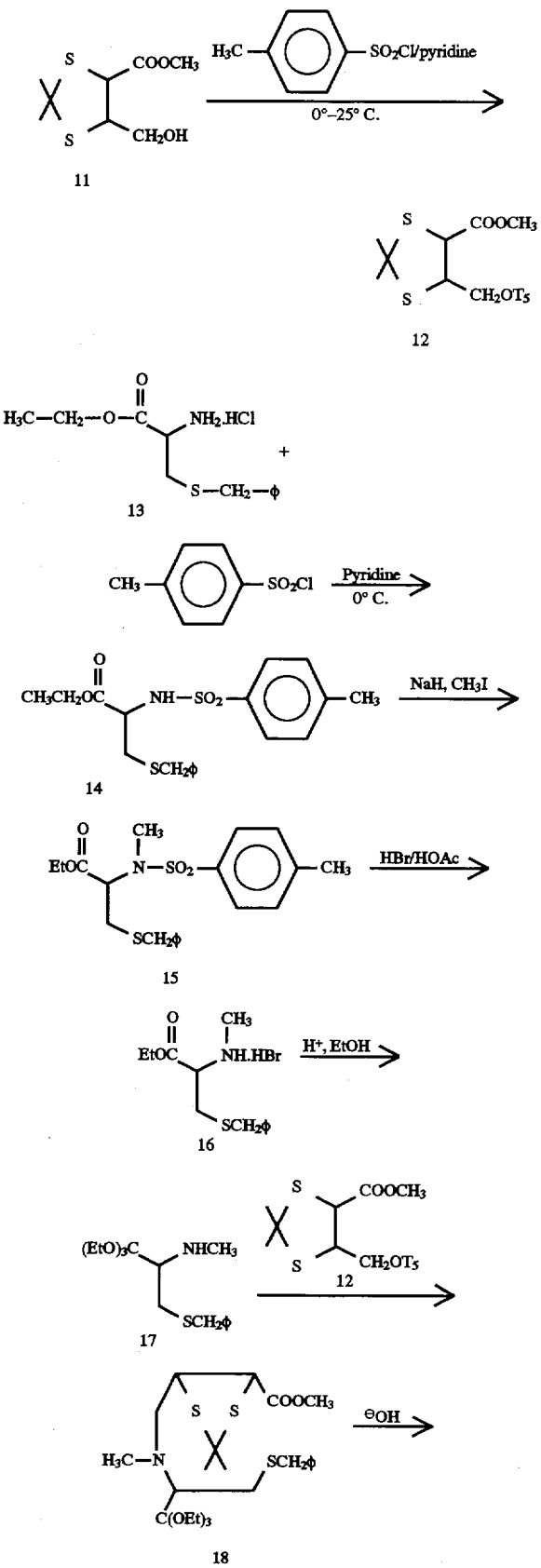

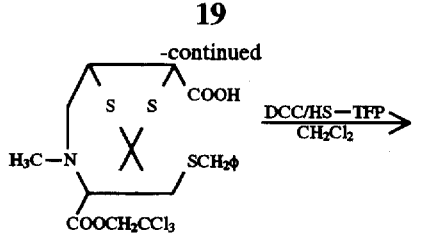

19

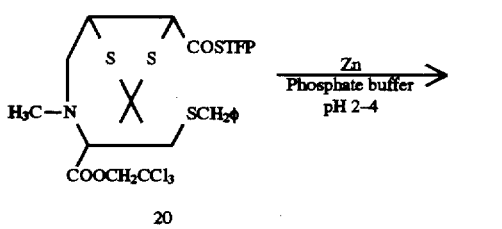

20

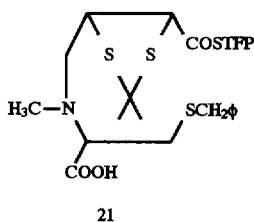

21

S,S'-Isopropylidene 2,3-dimercaptosuccinic acid (2)

To 1.0 g of meso 2,3-dimercaptosuccinic acid (DMSA), 50 mL of anhydrous acetone followed by 0.3 mL (6 drops) perchloric acid were added. The heterogeneous suspension was heated at 50° C. for 2 hours. Solvent from the clear light golden yellow solution was removed under reduced pressure. To the dried residue 50 mL water was added and extracted with ethyl acetate three times, each time with 100 mL. The combined ethyl acetate extracts were dried over anhydrous sodium sulfate and the solvent was removed in vacuo. The dry solid was dissolved in ether and the compound was precipitated by the addition of petroleum ether. The solid was filtered to give 0.9 g (74%) of 2 as a white compound which was recrystallized from CHCl₃/hexane to give crystals, MP 158°–160° C. $^1$H NMR (d$_6$ acetone) δ 4.85 (S,2H), δ 1.8, 1.9 (2S,6H).

S,S'-Isopropylidene 2,3-dimercaptosuccinic anhydride (3)

To 0.8 g (3.6 mmol) of S,S'-isopropylidene 2,3-dimercaptosuccinic acid (2), 10 mL of ethyl acetate was added. To this solution with stirring was added a solution of 1,3-dicyclohexylcarbodiimide 0.82 g (0.396 mmol) in 10 mL ethyl acetate. After stirring the reaction mixture at room temperature for two hours, the reaction mixture was filtered to remove the dicyclohexyl urea, a byproduct of the reaction. Removal of the solvent from the filtrate left a white solid. The crude product was purified by sublimation to give 0.52 g (71%) of S.S'-isopropylidene 2,3-dimercaptosuccinic anhydride (3), mp 141°–142° C. $^1$H NMR (d$_6$ acetone) δ 5.5 (S,2H), δ 1.8 (S,6H).

3-Carbomethoxy S,S'-isopropylidene 2,3-dimercaptopropionic acid (10)

Prepare a fresh 0.011 mol sodium methoxide in methanol solution by dissolving 0.26 g of sodium in 50 mL of anhydrous methanol. Then 1.0 g of S,S'-isopropylidene 2,3-dimercaptosuccinic anhydride is added to the reaction mixture and stirred at room temperature. Completion of the reaction is followed by thin layer chromatography. Add 25 mL of prewashed (water followed by methanol) BIORAD AG 50W-X4 (H$^+$) cation exchange resin and stir for 15 minutes. Then filter off the resin and wash it thoroughly with 25 mL methanol. Concentrate the filtrate to a residue on a rotatory evaporator. Add 15 mL heptane and evaporate the solvent to a dry residue to yield grey solid.

3-Carbomethoxy S,S'-isopropylidene 2,3-dimercaptopropanol (11)

To a solution of S,S'-isopropylidene 3-carbomethoxy 2,3-dimercaptopropionic acid in tetrahydrofuran at 35°–40° C. is rapidly added BH$_3$-THF (0.18 mmol). After three hours, an aliquot is analyzed by thin layer chromatography (ethyl acetate:hexane=4:1). Disappearance of the starting material is an indication of complete conversion to the alcohol. 10 mL of ethanol is added to the reaction mixture and the mixture is evaporated to dryness. After repeating the procedure twice with 20 mL of ethanol, the residue is suspended in water, extracted with ethyl acetate and the organic layer is washed successively with 2×15 mL of 2% aqueous bicarbonate and water followed by drying over anhydrous sodium sulfate. The organic solvent is then evaporated, the residue dissolved in hexane and upon cooling gives S,S'-isopropylidene 3-carbomethoxy 2,3-dimercaptopropanol (11) in high yield. The compound 10 to compound 11 tranformation may be preferably conducted employing a two-step synthetic procedure as shown below.

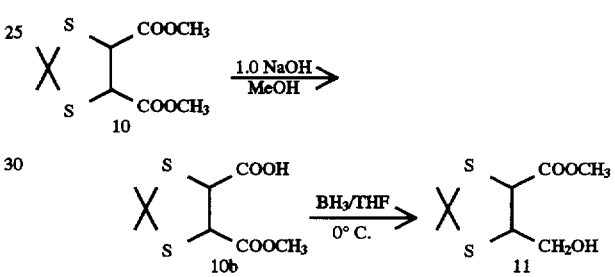

3-Carbomethoxy S,S'-isopropylidene 2,3-dimercaptopropionic acid 10 is treated with 1.0 equivalent of sodium hydroxide to hydrolyse the diester to the monoester (10b). The monoester is then reduced with borane at 0° C. to form S,S'-isopropylidene 3-carbomethoxy 2,3-dimercaptopropanol 11.

3-Carbomethoxy S,S'-isopropylidene 2,3-dimercaptopropanol tosylate (12)

The alcohol S,S'-isopropylidene 3-carbomethoxy 2,3-dimercaptopropanol (11, 1.0 g, 4.5 mmol) prepared above is dissolved in 5 mL of pyridine (0° C.–5° C.) and 0.9 g (4.7 mmol) of p-toluenesulfonyl chloride added at once. Precipitation of pyridinium hydrochloride is observed after one hour and the mixture is stirred for additional two hours, followed by storage at 4° C. overnight. The solution is poured with stirring into 50 mL of ice water and the resulting solid is isolated by filtration, washed with water and dried under vacuum in a desicator overnight to yield 60–80% of the tosyl ester, S,S'-isopropylidene 3-carbomethoxy 2,3-dimercaptopropanol tosyl ester, 12.

N-Tosyl-S-benzylcysteine ethyl ester (14)

S-benzylcysteine ethyl ester hydrochloride, 13 (5.0 g, 18.1 mmol) is dissolved in 25 ml of pyridine (0° C.–5° C.) and 3.5 g (18.3 mmol) of tosyl chloride is added at once. Precipitation of pyridinium hydrochloride is observed after one hour and the reaction mixture is stirred for an additional two hours, followed by storage at 4° C. overnight. The solution is poured with stirring into 150 mL of ice water and the resulting solid isolated by filtration, washed with ice cold water and dried under vacuum in a desicator overnight to yield 75–90% yield of S-benzyl cysteine ethyl ester tosylamide, 14. The crude product is recrystallized from ethyl acetate.

21

N-Tosyl-N-methyl S-benzylcysteine ethyl ester (15)

S-benzylcysteine ethyl ester tosylamide, 14 (5.0 g, 12.7 mmol) is dissolved in dimethylformamide. Solid sodium hydride (0.31 g, 12.9 mmol) is added. Then methyl iodide (1.9 g, 13.4 mmol) is added and the reaction mixture stirred at room temperature. Completion of the reaction is monitored by thin layer chromatography. Solvent from the reaction mixture is removed under vacuum and dried. The crude product is purified by flash chromatography to yield 50–75% of S-benzylcysteine ethyl ester N-methyltosylamide, 15.

S-Benz N-methylcysteine ethyl ester hydrobromide (16)

Glacial acetic acid is saturated with hydrogen bromide gas. To the stirred HBr solution one equivalent of solid S-benzylcysteine ethyl ester N-methyltosylamide is added. The reaction mixture is stirred at room temperature for 2 to 4 hours. Solvent from the reaction mixture is removed under reduced pressure and dried under vacuum to yield 75–80% of S-benzyl N-Methylcysteine ethyl ester hydrobromide salt 16.

S-Benzyl N-methylcysteine triethyl orthoester (17)

S-benzyl N-methylcysteine ethyl ester hydrobromide is converted to its triethyl orthoesther using acid catalyst by conventional method. Completion of the reaction is monitored by thin layer chromatography. The crude product is purified by flash chromatography.

N-Methyl-N-(β-benzylthio-α-triethoxmethyl)ethyl-S,S'-isopropylidene-2,3-dimercapto-4-aminobutyric acid methlyl ester (18)

S-benzyl N-methylcysteine triethylorthoester, 17 (3.0 g, 9.2 mmol) is dissolved in DMF. To the stirred solution at room temperature triethylamine (1.3 mL, 9.2 mmol) is added. Then, 3-carbomethoxy S,S'-isopropylidene 2,3-dimercaptopropanol tosylate, 12 (3.2 g, 9.2 mmol) is added and the reaction mixture is stirred at room temperature. The progress and completion of the reaction is followed by thin layer chromatography. Solvent from the reaction mixture is removed under vacuum and the resulting solid dried. The crude compound is purified by flash chromatography, to yield compound 18 in 60–80% yield.

N-Methyl-N-(β-benzylthio-α-trichloroethoxycarbonyl) ethyl-S,S'-isopropylidene-2,3-dimercapto-4-aminobutyric acid (19)

Compound 18 is hydrolyzed conventionally with 1 equivalent of sodium hydroxide to N-Methyl-N-(β-benzylthio-α-trichloroethoxycarbonyl)ethyl-S,S'-isopropylidene-2,3-dimercapto-4-aminobutyric acid, 19. The crude product is purified by flash chromatography.

N-Methyl-N-(β-benzylthio-α-trichloroethoxycarbonyl) ethyl-S,S'-isopropylidene-2,3-dimercapto-4-aminobutyric acid-2',3',5',6'-tetrafluorothiophenyl ester (20)

To a solution of compound 19 (1.0 g, 18.3 mmol) and 2,3,5,6-tetrafluorothiophenol (0.35 g, 21.08 mmol) in 25 mL dichloromethane is added 1,3-dicyclohexylcarbodiimide (0.45 g, 21.9 mmol) with rapid stirring. The mixture is stirred at room temperature for 18 to 24 hours, or until TLC analysis indicates complete conversion to the tetrafluorothiophenyl ester. Then the mixture is cooled to 0° C., a few drops of acetic acid is added, and the mixture is stirred for a few minutes and then filtered. The filtrate is concentrated under vacuum to give a solid. The solid is dissolved in minimum amount of methylene chloride and allowed to stand at 5° C. for two to three hours. The solution is then filtered to remove any precipitated dicyclohexyl urea, and the filtrate is concentrated to afford solid compound 20. The solid is then washed with ether to remove any remaining 2,3,5,6-tetrafluorothiophenol. The crude compound is purified by flash chromatography on silica gel column.

22

N-Methyl-N-(β-benzylthio-α-carboxy)ethyl-S,S'-isopropylidene-2,3-dimercapto-4-aminobutyric acid-2',3',5', 6'-tetrafluorothiophenyl ester (21)

To a solution of N-Methyl-N-(β-benzylthio-α-trichloroethoxycarbonyl)ethyl-S,S'-isopropylidene-2,3-dimercapto-4-aminobutyric acid-2,3',5',6'-tetrafluorothiophenyl ester 20 (0.5 g, 6.9 mmol) in 75 mL tetrahydrofuran, 1.4 mL of 1.0M $KH_2PO_4$ is added. To this solution, zinc dust (0.6 g, 91.9 mmol) is added. After stirring the reaction mixture at room temperature for 45 minutes, additional buffer (1.4 mL) and zinc dust (0.6 g) are added. The reaction mixture is sonicated for another hour. The TLC of the reaction mixture is an indication of completion of product formation. The mixture is sonicated for an additional hour. The reaction mixture is filtered, rinsed with acetonitrile, 50% $CH_3CN/H_2O$ with 1% acetic acid successively. The solvent is removed under reduced pressure. The residue is chromatographed on silica gel with 10% >—OH/ $CH_2Cl_2$-2% HOAC and then 25% >—OH/$CH_2Cl_2$-2% HOAC as elution solvents.

Compound 21 is a chelating compound of the present invention, also referred to as a ligand elsewhere herein. "COSTFP" represents a 2,3,5,6-tetrafluorothiophenyl ester, which is a conjugation group.

An alternative route to compound 21 is shown below.

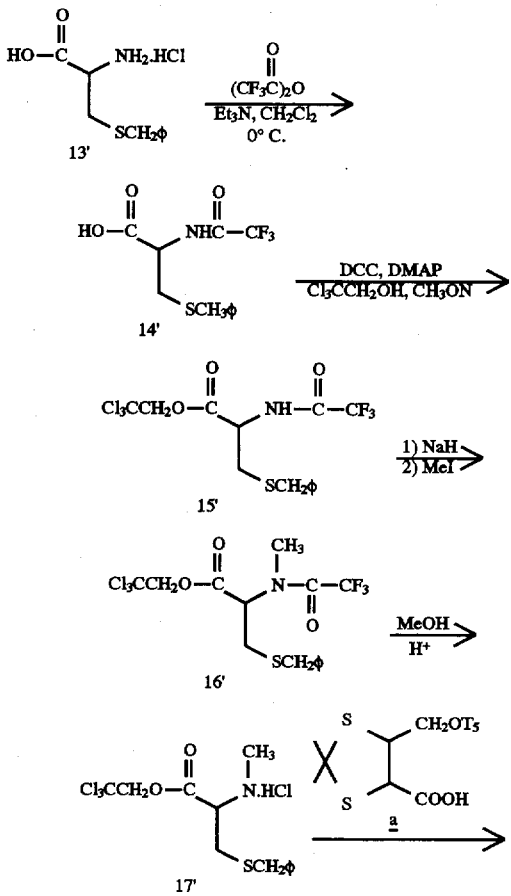

23

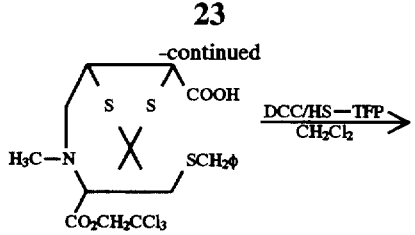

19

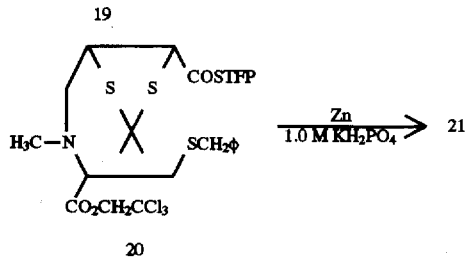

20

Compound a, utilized in the above synthetic scheme, is formed as shown below.

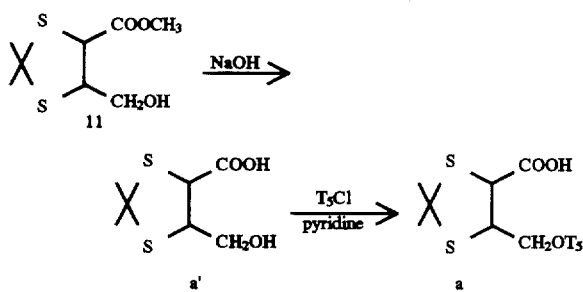

This alternative route begins with commercially available S-benzylcysteine (available from Aldrich Chemical Co., Milwaukee, Wis.), which is converted to trichloroethyl-N-methyl-S-benzylcysteine by established peptide protection/alkylation procedures. The protected N-methyl cysteine derivative is alkylated with the tosylate a in a step analogous to the original coupling of 17 and 12 to give 18. By using a instead of 12, the need to selectively hydrolyze the methyl ester in the presence of the protected carboxy group of 18 is avoided. Thus, the new route has the advantages of (1) incorporating the carboxy protecting group earlier in the synthesis which facilitates the formation of the tetrafluorothiophenyl ester and (2) simplifying thioester formation by protecting the 3-carboxyl propanol prior to incorporation of the dimercaptosuccinic acid portion of the molecule.

Trifluoroacetyl-S-benzyl cysteine (14')

Trifluoroacetic anhydride is added to a solution of S-benzylcysteine (13') in methylene chloride and triethylamine. The reaction mixture is stirred at 0° C. for one hour, acidified with 1.0M HCl and extracted with methylene chloride. The methylene chloride extracts are dried (MgSO₄) and evaporated to give 14'.

Trichloroethyl N-trifluoroacetyl-S-benzyl cysteine (15')

DCC is added to a solution of N-trifluoroacetyl-S-benzyl cysteine 14, trichloroethanol, and a catalytic amount of dimethylaminopyridine (DMAP) in acetonitrile. The reaction mixture is stirred at 23° C. for 12 hours, then is filtered to remove the DCU. The filtrate is evaporated to give 15'.

Trichloroethyl N-methyl-N-trifluoroacetyl-S-benzyl cysteine (16')

To a suspension of 15' and sodium hydride in DMF is added 1.0 equivalents methyl iodide. The reaction mixture is stirred at 23° C. for 12 hours and monitored by thin layer chromatography. The mixture is acidified carefully by the addition of acetic acid in DMF. The mixture is extracted with water and CH₂Cl₂. The CH₂Cl₂ extracts are dried (MgSO₄) and evaporated to give 16'. The product may be further purified by flash chromatography.

Trichloroethyl-S-benzyl-N-methyl cysteine (17')

The trifluoroacetyl group of 16' is cleaved by acidolysis. HCl gas is bubbled into a solution of 16' in methanol. The reaction is stirred at 23° C. for 12 hours or until thin layer chromatography shows that the reaction is complete. The methanol is evaporated to give 17'.

N-methyl-(beta-benzylthio-alpha-carboxy)ethyl-(S,S'-isopropylidene)-2,3-dimercapto-4-aminobutyric acid (19)

Trichloroethyl S-benzyl N-methyl cysteine 17' is dissolved in DMF. To the stirred solution at room temperature is added triethylamine. The 3-carboxy S,S'-isopropylidene-2,3-dimercapto propanol tosylate a, formed as described below, is added and the reaction mixture is stirred at room temperature. The progress and completion of the reaction is followed by thin layer chromatography. Solvent from the reaction mixture is removed under vacuum. The crude compound 19 is purified by flash chromatography.

3-Carboxy-(S,S'-isopropylidene-2,3-dimercaptopropanol tosylate (a)

To a solution of 3-carbomethoxy-S,S'-isopropylidene-2,3-dimercaptopropanol 11 in methanol is added 1–2 equivalents 1N NaOH. The solution is stirred at 23° C. for 4 hours or until the reaction is complete as indicated by thin layer chromatography. The solution is acidified by the addition of 1.0M HCl to pH 3, and concentrated. The residue is partitioned between ethyl acetate and water. The ethyl acetate is dried (MgSO₄) and evaporated to give 3-carboxy-(S,S'-isopropylidene)-2,3-dimercaptopropanol (a'). The alcohol a' is dissolved in pyridine at 0° C. and p-toluene sulfonyl chloride is added at once. The reaction mixture is stirred at 0° C. for 4 hours and then is stored over night at 4° C. The reaction solution is poured with stirring into ice water, and the resulting solid is isolated by filtration, washed with water and dried under vacuum in a dessicator over night to give the tosyl ester a.

N-Methyl-N-(β-benzylthio-α-trichloroethoxycarbonyl) ethyl-S,S'-isopropylidene-2,3-dimercapto-4-aminobutyric acid-2',3',5',6'-tetrafluorothiophenyl ester (20)

To a solution of compound 19 (1.0 g, 18.3 mmol) and 2,3,5,6-tetrafluorothiophenol (0.35 g, 21.08 mmol) in 25 mL dichloromethane is added 1,3-dicyclohexylcarbodiimide (0.45 g, 21.9 mmol) with rapid stirring. The mixture is stirred at room temperature for 18 to 24 hours, or until TLC analysis indicates complete conversion to the tetrafluorothiophenyl ester. Then the mixture is cooled to 0° C., a few drops of acetic acid is added, and the mixture is stirred for a few minutes and then filtered. The filtrate is concentrated under vacuum to give a solid. The solid is dissolved in minimum amount of methylene chloride and allowed to stand at 5° C. for two to three hours. The solution is then filtered to remove any precipitated dicyclohexyl urea, and the filtrate is concentrated to afford solid compound 20. The solid is then washed with ether to remove any remaining 2,3,5,6-tetrafluorothiophenol. The crude compound is purified by flash chromatography on silica gel column.

N-Methyl-N-(β-benzylthio-α-carboxy)ethyl-S,S'-isopropylidene-2,3-dimercapto-4-aminobutyric acid-2',3',5', 6'-tetrafluorothiophenyl ester (21)

To a solution of N-Methyl-N-(β-benzylthio-α-trichloroethoxycarbonyl)ethyl-S,S '-isopropylidene-2,3-dimercapto-4-aminobutyric acid-2',3',5',6'-tetrafluorothiophenyl ester 20 (0.5 g, 6.9 mmol) in 75 mL tetrahydrofuran, 1.4 mL of 1.0M KH₂PO₄ is added, preferably to pH 4–5. To this solution, zinc dust (0.6 g, 91.9 mmol) is added. After stirring the reaction mixture at room temperature for 45 minutes, additional buffer (1.4 mL) and zinc dust (0.6 g) are added. The reaction mixture is sonicated for another hour. The TLC of the reaction mixture is an indication of completion of product formation. The mixture is sonicated for an additional hour. The reaction mixture is filtered, rinsed with acetonitrile, 50% $CH_3CN/H_2O$ with 1% acetic acid successively. The solvent is removed under reduced pressure. The residue is chromatographed on silica gel with 10% >—$OH/CH_2Cl_2$-2% HOAC and then 25% >—$OH/CH_2C_2$-2% HOAC as elution solvents.

EXAMPLE II

Synthesis of a Chelating Compound

A chelating compound of the present invention was synthesized as generally depicted in the following reaction scheme:

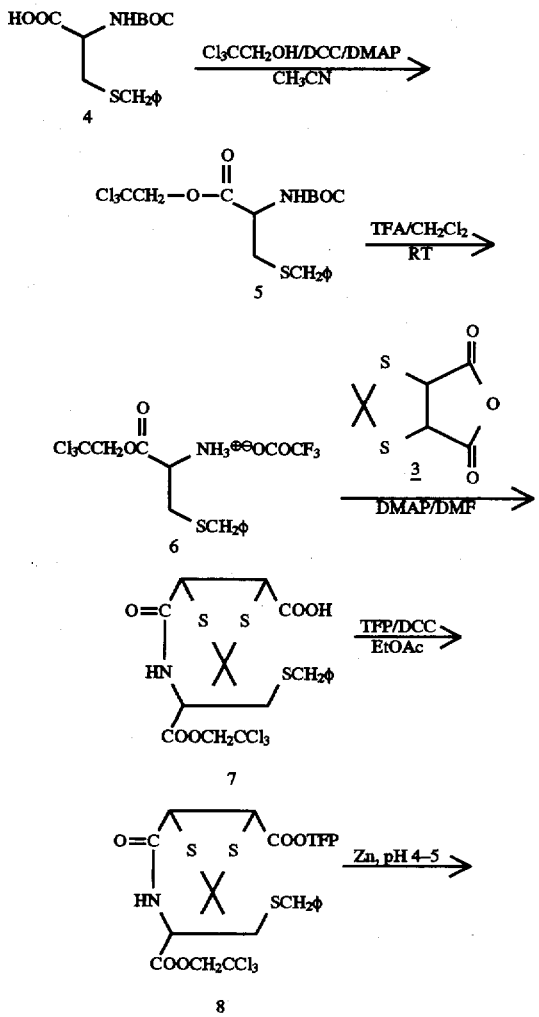

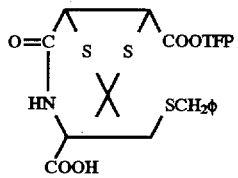

N-t-Butyloxycarbonyl S-benzyl L-cysteine trichloroethyl ester (5)

To an ice cold suspension of N-t-Butyloxycarbonyl S-benzyl cysteine 4 (5.0 g, 16.06 mmol) in 100 mL acetonitrile was added 4-dimethylaminopyridine (2.4 g, 19.6 mmol). To the solution was then added trichloroethanol (2.0 mL, 20.8 mmol). 1,3-dicyclohexylcarbodiimide (4.0 g, 19.4 mmol) was added as a solid. The ice bath was allowed to melt and the reaction mixture was stirred at room temperature for 15–18 hours. Analysis by thin layer chromatography indicated the reaction was complete. A few drops (8–10) of glacial acetic acid were added. The reaction mixture was cooled to 0° C. and the precipitate was filtered. The solvent from filtrate was removed in vacuo. The residue was dissolved in methylene chloride and washed with saturated sodium bicarbonate, brine, and water, respectively. Methylene chloride layer was dried over anhydrous sodium sulfate. After filtration and removal of solvent, a semi-solid was obtained which was purified by flash chromatography on a silica gel column using methylene chloride as an elution solvent to give 3.0 g of 5: $^1$H NMR ($d_6$-DMSO) 1.39 (S,9H), 2.6–2.9 (m,2H), 3.75 (S,2H), 4.15–4.35 (M,1H), 4.75–5.0 (Q,2H), 7.25 (S,5H), 7.40–7.55 (d, 1H).

S-Benzyl cysteine 1,1,1-trichloroethylester trifluoroacetate (6)

1,1,1-trichloroethyl N-t-Butyloxycarbonyl S-benzyl cysteinate (1.5 g, 3.0 mmol) was dissolved in 10 mL methylene chloride. To the clear solution, 10 mL of trifluoroacetic acid was added and the reaction mixture was stirred at room temperature for one hour. Completion of the reaction was also monitored by thin layer chromatography on silica gel plates using methylene chloride as developing solvent. The solvent was removed under reduced pressure. The solid residue was washed twice with heptane and the solvent was removed under vacuum to give 1.5 g. The residue was dried under vacuum and used for further reactions without purification.

N-(3-Carboxy-S,S'-isopropylidene-2,3-dimercapto) propionyl-S-benzylcysteine trichloroethyl ester (7)

To a solution of trichloroethyl S-benzylcysteine trifluoroacetate (1.54 g, 3.4 mmol) in 10 mL anhydrous dimethylformamide was added a solution of isopropylidene 2,3-dimercaptosuccinic anhydride (0.75 g, 3.7 mmol) in 10 mL dimethylformamide. To the reaction mixture was then added dimethylaminopyridine (1.0 g, 8.2 mmol) as a dry solid. The reaction mixture was stirred at room temperature overnight. The DMF from the reaction mixture was removed at low heat under vacuum. The semi-solid residue was dried and purified by flash chromatography on a silica gel column using ethyl acetate and ethyl acetate:acetic acid (98:2) as elution solvents successively.

N-(b 3-(2',3',5',6'-tetrafluorophenoxycarbonyl)-S,S'-isopropylidene-2,3-dimercapto)propionyl-S-benzylcysteine trichloroethyl ester (8)

To a solution of compound 7 (0.5 g, 0.0009 mol) and 2,3,5,6-tetrafluorophenol (0.3 g, 0.0018 mol) in 15 mL dichloromethane is added 1,3-dicyclohexyl carbodiimide (0.3 g, 0.0015 mol) with rapid stirring. The mixture is stirred at room temperature for 2 to 4 hours or until TLC analysis indicated complete conversion to the tetrafluorophenyl ester. Then the mixture is cooled to 0° C., a few drops of acetic acid are added, the mixture stirred for a few minutes, and then is filtered. The filtrate is concentrated under vacuum to give solid. The solid is dissolved in minimum amount of methylene chloride and allowed to stand at 5° C. for two to three hours. The solution is then filtered to remove any precipitated dicyclohexyl urea, and the filtrate is concentrated to afford solid N-(3-(2',3',5',6'-tetrafluorophenoxycarbonyl-S,S'-isopropylidene-2,3-dimercapto)propionyl-S-benzylcysteine trichloroethyl ester. The solid is then either washed with ether to remove any remaining 2,3,5,6-tetrafluorophenol or purified by flash chromatography on silica gel using $CH_2C_2$:IPA:HOAC= 90:5:5 as elution solvent. The solvent from eluent is removed under vacuum and dried.

N-(3-(2',3',5',6'-tetrafluorophenoxycarbonyl)-S,S'-isopropylidene-2,3-dimercapto)propionyl-S-benzylcysteine (9)

To a solution of compound 8 (0.21 g, 0.0003 mol) in 75 mL tetrahydrofuran, 0.56 mL of 1.0M $KH_2PO_4$ is added. To this solution, zinc dust (0.275 g, 0.004 mol) is added. After stirring the reaction mixture at room temperature for 45 minutes, additional buffer (0.56 mL) and zinc dust (0.275 g) are added. The reaction mixture is sonicated for another hour. The TLC of the reaction mixture is an indication of completion of product formation. The mixture is sonicated for an additional hour. The reaction mixture is filtered, then rinsed with acetonitrile, 50% $CH_3CN/H_2O$ with 1% acetic acid successively. The solvent is removed under reduced pressure. The residue is chromatographed on silica gel with 10% >—$OH/CH_2Cl_2$-2% HOAC and then 25% >—OH/ $CH_2Cl_2$-2% HOAC as elution solvents.

Compound 9 is a chelating compound of the present invention, also referred to as a ligand elsewhere herein. "COOTFP" represents a 2,3,5,6-tetrafluorophenyl ester, which is a conjugation group. It is to be noted that the thioacetal portion of the chelating compound may also be shown as:

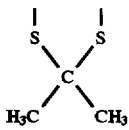

(the two different representations being equivalent).

EXAMPLE III

Conjugation of 2,3,5,6-Tetrafluorophenyl S-benzyl Cysteino 2,3-Dimercaptosuccinamidate to an Antibody The antibody used for derivatization is a monoclonal antibody fragment designated NR-LU-10 Fab, a murine antibody specific for human carcinoma surface antigen. The antibody is functionalized by dissolving the ligand, 2,3,5,6-tetrafluorophenyl S-benzyl cysteino 2,3-dimercaptosuccinamidate (compound 9 prepared in example II), in dimethylformamide solvent during derivatization with 70:1 molar offering of ligand to antibody. 100 µL of 20 mg/mL NR-LU-10 Fab in phosphate buffered saline is mixed with 300 µL of 0.2M phosphate buffer, pH 9.5. To the buffered antibody solution, 30 µL of 2.0 mg/mL ligand solution in DMF is added. The reaction mixture is incubated at room temperature for one hour. The resulting antibody-ligand conjugate is purified by size exclusion chromatography using a sephadex G-25 (PD-10) reversed phase column equilibrated with 0.2M sodium acetate buffer, pH 5.0. The 2.4–4.8 mL fractions off the PD-10 column are collected and used for radiolabeling with $_{99m}$Tc.

The antibody-ligand (i.e., chelating compound) conjugate is believed to be of the following chemical structure:

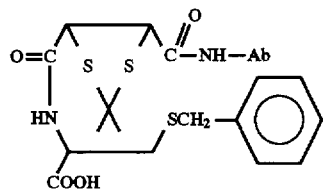

wherein Ab represents the antibody fragment and

is the amide bond formed by reaction of a primary amine on a lysine residue of the antibody with the active ester conjugation group on the chelating compound.

Chelating compound 21, produced in Example I, may be substituted for compound 9 in the procedures above to produce an antibody-ligand conjugate of the formula:

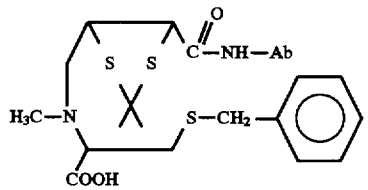

EXAMPLE IV

Preparation of Radiolabeled Proteins Tc-99m Radiolabeling of Antibody-ligand Conjugate To 100 µL of a solution containing 5 mg of sodium gluconate and 0.1 mg of stannous chloride in water, 1.0 mL of $^{99m}TcO_4^-$ (pertechnetate) is added. After incubation at room temperature for one minute to form a $^{99m}$Tc-gluconate intermediate exchange complex, 200 µL of the $^{99m}$Tc-gluconate solution is mixed with 525 µL of freshly prepared PD-10 purified antibody-ligand conjugate (0.44 mg antibody-ligand conjugate prepared in example III). The reaction mixture is incubated at 37° C. for 15 minutes. The percentage of the Tc-99m from Tc-gluconate bound to the antibody-ligand conjugate is determined by standard instant thin layer chromatography (ITLC) in 12% trichloroacetic acid as a developing solvent. The native antibody fragment underivatized with ligand is used as a control. Minimal Tc-99m uptake in the control experiment is an indication that the Tc-99m uptake by the antibody-ligand conjugate is specific for the ligand and that non-specific Tc-99m uptake is negligible.

$^{188}$Re Chelates

The same chelating compound may be radiolabeled with $^{188}$Re by a procedure similar to the $^{99m}$Tc labeling procedure. Sodium perrhenate produced from a W-188/Re-188 research scale generator is combined with citric acid (a preferred complexing agent for $^{188}$Re), a reducing agent, and preferably gentisic acid and lactose. The resulting $^{188}$Re-citrate exchange complex is reacted with the desired chelating compound-antibody conjugate, as above. A Sephadex G-25 column may be used to purify the radiolabeled antibody. A $^{186}$Re-citrate exchange complex may be substituted in the same procedure.

The resulting radiolabeled antibodies (produced using antibody conjugates of ligands 9 and 21, respectively) are believed to have the following structures:

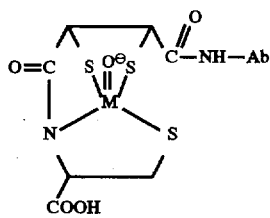

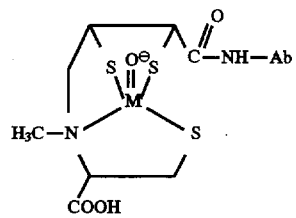

wherein M represents a radionuclide metal selected from $^{99m}$Tc, $^{188}$Re, and $^{186}$Re. Ab represents the antibody fragment, and

is the amide bond formed by the reaction of the primary amine on a lysine residue of the antibody with the active ester conjugation group on the chelating compound.

Other chelating compounds of formulas I and II may be attached to an antibody fragment and radiolabeled using the same procedures described above for chelating compounds 9 and 21. Other targeting proteins may be substituted for the antibody fragment in these procedures.

EXAMPLE V

Radiolabeled Ligand Preparation

A. One synthetic route for a S$_3$N-biotin conjugate is shown below:

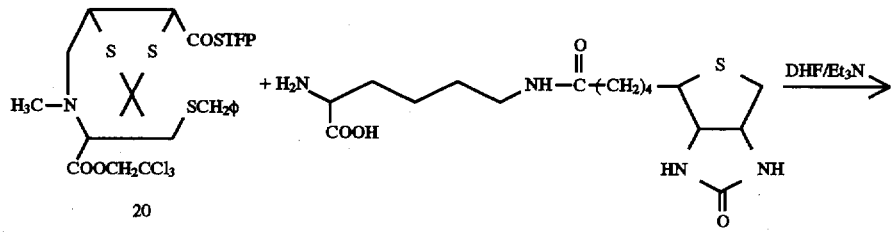

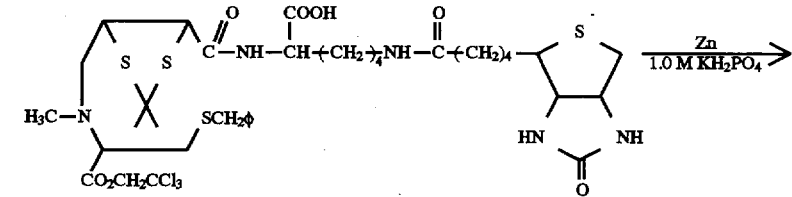

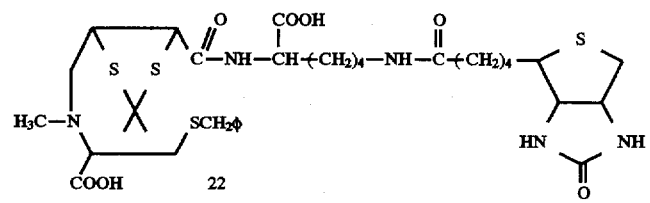

N-[4-biocytinamido-(S,S'-isopropylidine-2,3-dimercatptol butyryl-S-S-benzyl trichloroethyl cysteine (21')

The tetrafluorothiophenyl ester 20, as previously described, and biocytin (commercially available from Sigma Chemical Co., St. Louis, Mo.) are stirred in DMF and triethylamine. The progress of the reaction is monitored by thin layer chromatography. If the reaction does not go to completion, the solution is heated at 80° C. for 30 minutes. After thin layer chromatography indicates reaction completion, the DMF is evaporated. The residue is purified by chromatography to afford 21'.

N-Methyl-N-[4-biocytinamido-(S,S'-isopropylidene-2,3-dimercapto]butyryl-S-benzyl cysteine (22)

To a solution of 21' in THF and 1.0M $KH_2PO_4$ is added zinc dust. After 30 minutes, additional 1.0M $KH_2PO_4$ and zinc dust are added. The mixture is sonicated for 1 hour, then filtered, rinsed with $CH_3CN$, 50% $CH_3CN/H_2O$. The filtrate is evaporated under vacuum. The residue is chromatographed on silica gel to afford the product 22.

B. Another synthetic route for a $S_3N$-biotin conjugate is shown below.

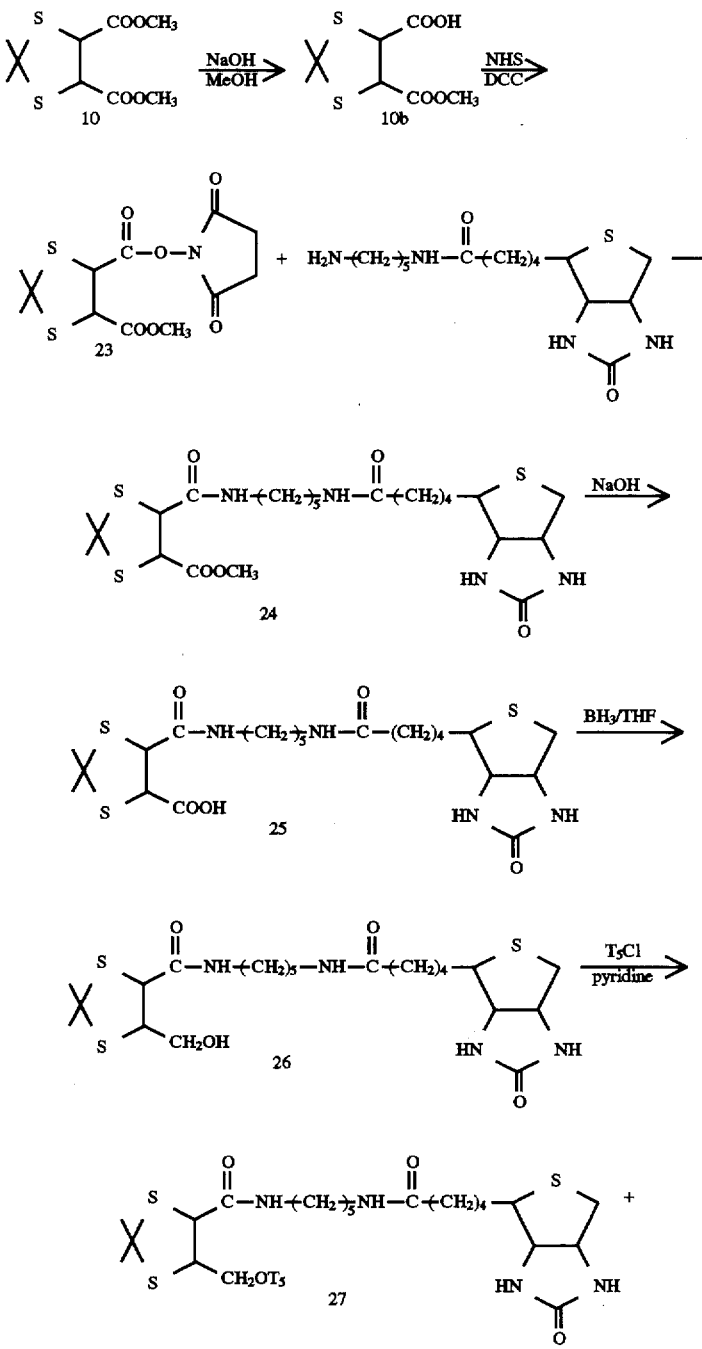

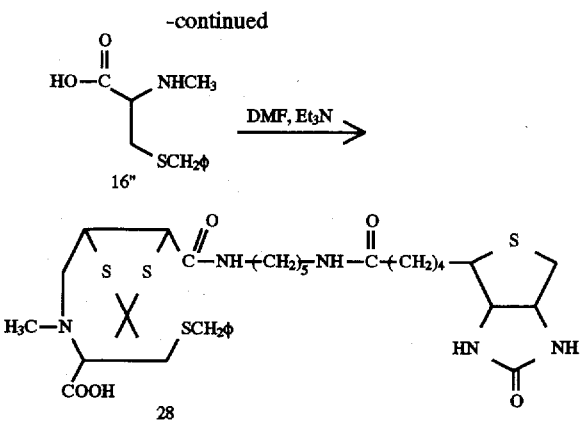

This route is preferred over that described in Section A of this Example for the following reasons: (1) the route has fewer synthetic steps; (2) biotin is introduced earlier in the synthesis and, therefore, orthogonal protection of the cysteine carboxylic acid is not required; and (3) the amide bond linking biocytin to succinic acid is formed from a monocarboxylate 10b, rather than by selective acylation of the diester 20 of the previously discussed route.

Monomethyl-(S,S'-isoropropylidene-2,3-dimercaptosuccinate (10b)

To a solution of dimethyl-S,S'-isopropylidene-2,3-dimercaptosuccinate 10 in methanol is added 1–2 equivalents 1N NaOH. The solution is stirred at 23° C. for 4 hours or until the reaction is complete as indicated by thin layer chromatography. The solution is acidified by the addition of 1.0M HCl to pH 3 and then concentrated. The residue is partitioned between ethyl acetate and water. The ethyl acetate is dried (MgSO$_4$) and evaporated to give 10b.

N-hydroxysuccinimidyl-methyl-S,S'-isopropylidene)-2,3-dimercaptosuccinate (23)

To a solution of 10b in acetonitrile is added NHS and DCC. The reaction is stirred at 23° C. for 4 hours and filtered to remove DCU. The filtrate is evaporated to give the NHS ester product 23.

(5-Biotinamido)-pentylamido-methyl-S,S'-isopropylidene)-2,3-dimercaptosuccinate (24)

A solution of 5-biotinamido-pentylamine (available from Pierce Chemical Company) and 23 in DMF and triethylamine is stirred at 23° C. for 4 hours. The progress of the reaction is monitored by thin layer chromatography. If the reaction is not progressing, the reaction mixture is heated at 80° C. for 30 minutes. The solvent is removed under vacuum upon completion of the reaction. The residue is purified by flash chromatography.

5-biotinamido)-pentylamido-S,S'-isopropylidene)2,3-dimercaptosuccinate 25

To a solution of 24 in methanol is added 1–2 equivalents of 1N NaOH. The solution is stirred at 23° C. for 4 hours or until the reaction is complete as analyzed by thin layer chromatography. The solution is acidified by the addition of 1.0M HCl to pH 3 and then concentrated. The residue is dried and used without further purification.

3-[(5-Biotinamido)-pentylamido]-S,S'-isopropylidene-2,3-dimercapto-propanol 26

To an ice cold solution of 25 in THF is added 1.0M borane in THF. The reaction is stirred at 0° C. for 4 hours and then quenched by the addition of methanol. The solution is evaporated. The residue is dissolved in methanol and evaporated. The residue is redissolved in methanol and evaporated. The residue is purified by flash chromatography to afford the product 26.

3-[(5-Biotinamido)-pentylamido]-S,S'-isopropylidene)-2,3-dimercapto-propanol toluene sulfonate 27

Para-toluene sulfonyl chloride is added to an ice cold solution of 26 in pyridine. The reaction is stirred at 0° C. for 4 hours and then stored over night at 4° C. The reaction mixture is poured with stirring into ice water, and the resulting solid is isolated by filtration, washed with water and dried under vacuum in a dessicator over night to give the tosyl ester 27.

N-[[(5-Biotinamido-pentylamido]-S,S'-isopropylidene-)-2,3-dimercapto]butyryl-S-benzyl cysteine 28

In a manner analogous to the procedure described above for the preparation of trichloroethyl-N-methyl-S-benzyl cysteine 17', N-methyl-S-benzyl cysteine 16" is prepared and is employed to produce 28 as shown and then described below.

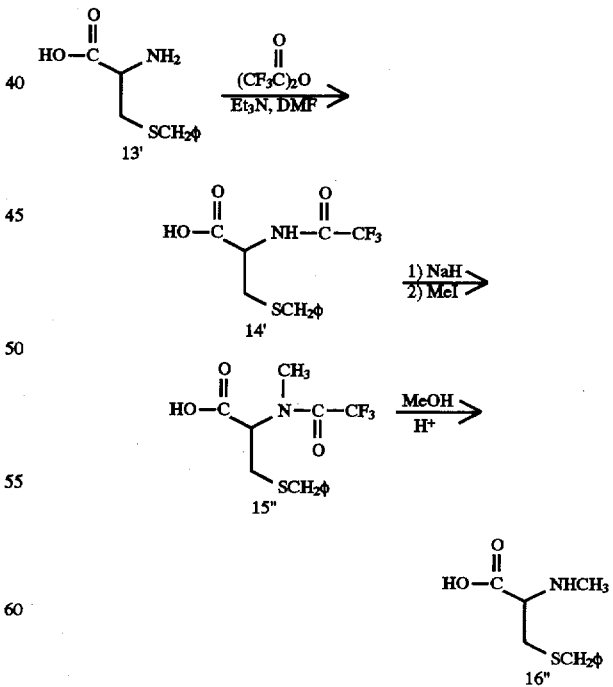

To a suspension of N-trifluoroacetyl-S-benzyl cysteine 14' and sodium hydride in DMF is added 1.0 equivalents methyl iodide. The reaction mixture is stirred at 23° C. for 12 hours and monitored by thin layer chromatography. The mixture is quenched by the addition of water and acidified by the addition of 1.0M HCl. The solution is evaporated. The residue is partitioned between ethyl acetate and water. The ethyl acetate extracts are dried (MgSO₄), filtered and evaporated. If necessary, the product, N-methyl-N-trifluoroacetyl-S-benzyl cysteine 15" is further purified by column chromatography.

The trifluoroacetyl group of 15" is cleaved by acidolysis. HCl gas is bubbled into a solution of 15" in methanol. The reaction is stirred at 23° C. for 12 hours or until thin layer chromatography shows that the reaction is complete. The methanol is evaporated to give S-benzyl-N-methyl cysteine 16".

16" is dissolved in DMF and triethylamine. To the stirred solution at 23° C. is added the tosylate 27. The progress and completion of the reaction is followed by thin layer chromatography. The reaction solution is concentrated under vacuum. The crude product is purified by flash chromatography.

C. A third S₃N-biotin conjugate synthetic scheme is shown below.

[(5-Biotinamido)-pentylamido]-S,S'-isopropylidene)-2,3-dimercaptosuccinate 29

To a solution of 3 in DMF is added a solution of 5-biotinamido-pentylamine (available from Pierce Chemical Company) in DMF. To the reaction mixture is then added dimethylaminopyridine as a dry solid. The mixture is stirred at 23° C. for 12 hours. The DMF is removed under vacuum. The residue is purified by flash chromatography on silica gel.

N-hydroxysuccinimidyl-[5-biotinamido-pentylamido]-(S,S'-isopropylidene)-2,3-dimercaptosuccinate 30

To a solution of the carboxylic acid 29 in DMF is added NHS and DCC. The reaction is stirred at 23° C. for 4 hours and is then filtered to remove DCU. The DMF is evaporated. The crude NHS ester is used without purification.

(S-benzyl)-cysteinyl-[5-biotinamido)-pentylamido]-(S,S'-isopropylidene-2,3-dimercaptosuccinate 31

To an equimolar solution of S-benzylcysteine (available from Aldrich Chemical Company, Milwaukee, Wis.) the N-hydroxy-succinimidyl ester 30 in DMF is added triethylamine. The solution is stirred at 23° C. for 12 hours and is then concentrated under vacuum. The residue is purified by flash chromatography to give the final product.

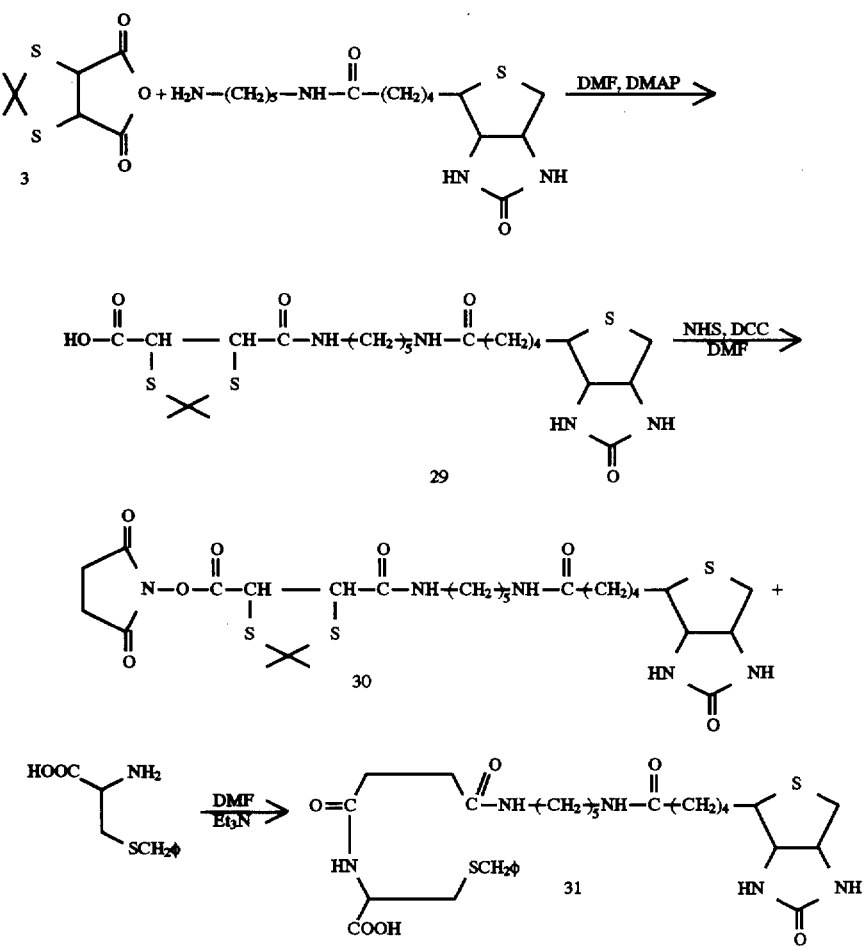

D. A fourth reaction scheme useful in the production of S₃N-biotin conjugates is shown below.

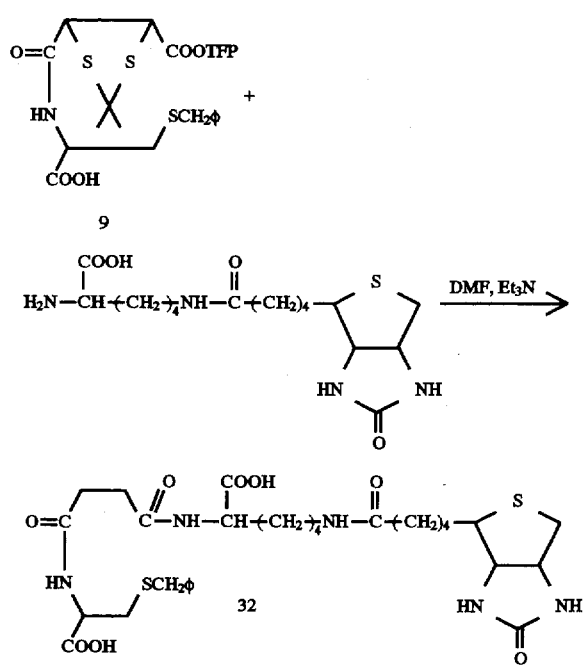

Biocytinamido-(S-benzyl)-cysteinyl-(S,S'-isopropylidene)-2,3-dimercaptosuccinate 32

A solution of biocytin (available from Sigma Chemical Company) and 9 in DMF and triethylamine is stirred at 23° C. for 4 hours. The progress of the reaction is monitored by thin layer chromatography. If the reaction is not progressing, the reaction solution is heated at 80° C. for 30 minutes. The DMF is removed under vacuum. The residue is purified by chromatography.

EXAMPLE VI

Preparation of Targeting Moiety-Ligand and Targeting Moiety-Anti-Ligand Conjugates A. Preparation and Characterization of Biotinylated Antibody Biotinylated NR-LU-10 was prepared according to either of the following procedures. The first procedure involved derivitization of antibody via lysine ε-amino groups. NR-LU-10 was radioiodinated at tyrosines using chloramine T and either $^{125}I$ or $^{131}I$ sodium iodide. The radioiodinated antibody (5–10 mg/ml) was then biotinylated using biotinamido caproate NHS ester in carbonate buffer, pH 8.5, containing 5% DMSO, according to the scheme below.

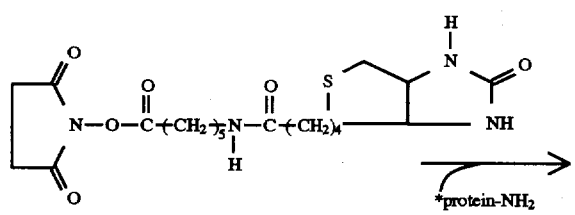

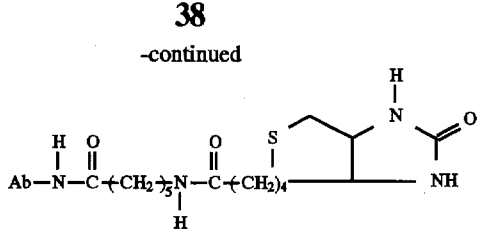

The impact of lysine biotinylation on antibody immunoreactivity was examined. As the molar offering of biotin:antibody increased from 5:1 to 40:1, biotin incorporation increased as expected (measured using the HABA assay and pronase-digested product) (Table 1, below). Percent of biotinylated antibody immunoreactivity as compared to native antibody was assessed in a limiting antigen ELISA assay. The immunoreactivity percentage dropped below 70% at a measured derivitization of 11.1:1; however, at this level of derivitization, no decrease was observed in antigen-positive cell binding (performed with LS-180 tumor cells at antigen excess). Subsequent experiments used antibody derivitized at a biotin:antibody ratio of 10:1.

TABLE 1

| Effect of Lysine Biotinylation on Immunoreactivity | | | |
|---|---|---|---|
| Molar Offering | Measured Derivitization | Immunoassessment (%) | |
| (Biotins/Ab) | (Biotins/Ab) | ELISA | Cell Binding |
| 5:1 | 3.4 | 86 | |
| 10:1 | 8.5 | 73 | 100 |
| 13:1 | 11.1 | 69 | 102 |
| 20:1 | 13.4 | 36 | 106 |
| 40:1 | 23.1 | 27 | |

Alternatively, NR-LU-10 was biotinylated using thiol groups generated by reduction of cystines. Derivitization of thiol groups was hypothesized to be less compromising to antibody immunoreactivity. NR-LU-10 was radioiodinated using p-aryltin phenylate NHS ester (PIP-NHS) and either $^{125}I$ or $^{131}I$ sodium iodide. Radioiodinated NR-LU-10 was incubated with 25 mM dithiothreitol and purified using size exclusion chromatography. The reduced antibody (containing free thiol groups) was then reacted with a 10- to 100-fold molar excess of N-iodoacetyl-n'-biotinyl hexylene diamine in phosphate-buffered saline (PBS), pH 7.5, containing 5% DMSO (v/v).

TABLE 2

| Effect of Thiol Biotinylation on Immunoreactivity | | | |
|---|---|---|---|
| Molar Offering | Measured Derivitization | Immunoassessment (%) | |
| (Biotins/Ab) | (Biotins/Ab) | ELISA | Cell Binding |
| 10:1 | 4.7 | 114 | |
| 50:1 | 6.5 | 102 | 100 |
| 100:1 | 6.1 | 95 | 100 |

As shown in Table 2, at a 50:1 or greater biotin:antibody molar offering, only 6 biotins per antibody were incorporated. No significant impact on immunoreactivity was observed.

The lysine- and thiol-derivitized biotinylated antibodies ("antibody (lysine)" and "antibody (thiol)", respectively)

were compared. Molecular sizing on size exclusion FPLC demonstrated that both biotinylation protocols yielded monomolecular (monomeric) IgGs. Biotinylated antibody (lysine) had an apparent molecular weight of 160 kD, while biotinylated antibody (thiol) had an apparent molecular weight of 180 kD. Reduction of endogenous sulfhydryls to thiol groups, followed by conjugation with biotin, may produce a somewhat unfolded macromolecule. If so, the antibody (thiol) may display a larger hydrodynamic radius and exhibit an apparent increase in molecular weight by chromatographic analysis. Both biotinylated antibody species exhibited 98% specific binding to immobilized avidin-agarose.

Further comparison of the biotinylated antibody species was performed using non-reducing SDS-PAGE, using a 4% stacking gel and a 5% resolving gel. Biotinylated samples were either radiolabeled or unlabeled and were combined with either radiolabeled or unlabeled avidin or streptavidin. Samples were not boiled prior to SDS-PAGE analysis. The native antibody and biotinylated antibody (lysine) showed similar migrations; the biotinylated antibody (thiol) produced two species in the 50–75 kD range. These species may represent two thiol-capped species. Under these SDS-PAGE conditions, radiolabeled streptavidin migrates as a 60 kD tetramer. When 400 μg/ml radiolabeled streptavidin was combined with 50 μg/ml biotinylated antibody (analogous to "sandwiching" conditions in vivo), both antibody species formed large molecular weight complexes. However, only the biotinylated antibody (thiol)-streptavidin complex moved from the stacking gel into the resolving gel, indicating a decreased molecular weight as compared to the biotinylated antibody (lysine)-streptavidin complex.

B. Blood Clearance of Biotinflated Antibody Species

Radioiodinated biotinylated NR-LU-10 (lysine or thiol) was intravenously administered to non-tumored nude mice at a dose of 100 μg. At 24 h post-administration of radioiodinated biotinylated NR-LU-10, mice were intravenously injected with either saline or 400 μg of avidin. With saline administration, blood clearances for both biotinylated antibody species were biphasic and similar to the clearance of native NR-LU-10 antibody.

In the animals that received avidin intravenously at 24 h, the biotinylated antibody (lysine) was cleared (to a level of 5% of injected dose) within 15 min of avidin administration (avidin:biotin=10:1). With the biotinylated antibody (thiol), avidin administration (10:1 or 25:1) reduced the circulating antibody level to about 35% of injected dose after two hours. Residual radiolabeled antibody activity in the circulation after avidin administration was examined in vitro using immobilized biotin. This analysis revealed that 85% of the biotinylated antibody was complexed with avidin. These data suggest that the biotinylated antibody (thiol)-avidin complexes that were formed were insufficiently crosslinked to be cleared by the RES.

Blood clearance and biodistribution studies of biotinylated antibody (lysine) 2 h post-avidin or post-saline administration were performed. Avidin administration significantly reduced the level of biotinylated antibody in the blood, and increased the level of biotinylated antibody in the liver and spleen. Kidney levels of biotinylated antibody were similar.

C. of Biotinylated Antibody (Thiol) Through Endogenous Antibody Sulfhydryl Groups Or Sulfhydryl-Generating Compounds Certain antibodies have available for reaction endogenous sulfhydryl groups. If the antibody to be biotinylated contains endogenous sulfhydryl groups, such antibody is reacted with N-iodoacetyl-n'-biotinyl hexylene diamine. The availability of one or more endogenous sulfhydryl groups obviates the need to expose the antibody to a reducing agent, such as DTT, which can have other detrimental effects on the biotinylated antibody.

Alternatively, one or more sulfhydryl groups are attached to a targeting moiety through the use of chemical compounds or linkers that contain a terminal sulfhydryl group. An exemplary compound for this purpose is iminothiolane. As with endogenous sulfhydryl groups (discussed above), the detrimental effects of reducing agents on antibody are thereby avoided.

D. Targeting Moiety-Anti-Ligand Conjugate for Two-Step Pretargeting

1. Preparation of SMCC-derivitized streptavidin.

31 mg (0.48 μmol) streptavidin was dissolved in 9.0 ml PBS to prepare a final solution at 3.5 mg/ml. The pH of the solution was adjusted to 8.5 by addition of 0.9 ml of 0.5M borate buffer, pH 8.5. A DMSO solution of SMCC (3.5 mg/ml) was prepared, and 477 μl (4.8 μmol) of this solution was added dropwise to the vortexing protein solution. After 30 minutes of stirring, the solution was purified by G-25 (PD-10, Pharmacia, Piscataway, N.J.) column chromatography to remove unreacted or hydrolyzed SMCC. The purified SMCC-derivitized streptavidin was isolated (28 mg, 1.67 mg/ml).

2. Preparation of DTT-reduced NR-LU-10. To 77 mg NR-LU-10 (0.42 μmol) in 15.0 ml PBS was added 1.5 ml of 0.5M borate buffer, pH 8.5. A DTT solution, at 400 mg/ml (165 μl) was added to the protein solution. After stirring at room temperature for 30 minutes, the reduced antibody was purified by G-25 size exclusion chromatography. Purified DTT-reduced NR-LU-10 was obtained (74 mg, 2.17 mg/ml).

3. Conjugation of SMCC-streptavidin to DTT- reduced NR-LU-10. DTT-reduced NR-LU-10 (63 mg, 29 ml, 0.42 μmol) was diluted with 44.5 ml PBS. The solution of SMCC-streptavidin (28 mg, 17 ml, 0.42 μmol) was added rapidly to the stirring solution of NR-LU-10. Total protein concentration in the reaction mixture was 1.0 mg/ml. The progress of the reaction was monitored by HPLC (Zorbax® GF-250, available from MacMod). After approximately 45 minutes, the reaction was quenched by adding solid sodium tetrathionate to a final concentration of 5 mM.

4. Purification of conjugate. For small scale reactions, monosubstituted conjugate was obtained using HPLC Zorbax (preparative) size exclusion chromatography. The desired monosubstituted conjugate product eluted at 14.0–14.5 min (3.0 ml/min flow rate), while unreacted NR-LU-10 eluted at 14.5–15 min and unreacted derivitized streptavidin eluted at 19–20 min.

For larger scale conjugation reactions, monosubstituted adduct is isolatable using DEAE ion exchange chromatography. After concentration of the crude conjugate mixture, free streptavidin was removed therefrom by eluting the column with 2.5% xylitol in sodium borate buffer, pH 8.6. The bound unreacted antibody and desired conjugate were then sequentially eluted from the column using an increasing salt gradient in 20 mM diethanolamine adjusted to pH 8.6 with sodium hydroxide.

5. Characterization of Conjugate.
  a. HPLC size exclusion was conducted as described above with respect to small scale purification.
  b. SDS-PAGE analysis was performed using 5% polyacrylamide gels under non-denaturing conditions. Conjugates to be evaluated were not boiled in sample buffer containing SDS to avoid dissociation of streptavidin into its 15 kD subunits. Two product bands were observed on the gel, which correspond to the mono- and di-substituted conjugates.

c. Immunoreactivity was assessed, for example, by competitive binding ELISA as compared to free antibody. Values obtained were within 10% of those for the free antibody.

d. Biotin binding capacity was assessed, for example, by titrating a known quantity of conjugate with p-[I-125] iodobenzoylbiocytin. Saturation of the biotin binding sites was observed upon addition of 4 equivalences of the labeled biocytin.

e. In vivo studies are useful to characterize the reaction product, which studies include, for example, serum clearance profiles, ability of the conjugate to target antigen-positive tumors, tumor retention of the conjugate over time and the ability of a biotinylated molecule to bind streptavidin conjugate at the tumor. These data facilitate determination that the synthesis resulted in the formation of a 1:1 streptavidin-NR-LU-10 whole antibody conjugate that exhibits blood clearance properties similar to native NR-LU-10 whole antibody, and tumor uptake and retention properties at least equal to native NR-LU-10.

For example, FIG. 1 depicts the tumor uptake profile of the NR-LU-10-streptavidin conjugate (LU-10-StrAv) in comparison to a control profile of native NR-LU-10 whole antibody. LU-10-StrAv was radiolabeled on the streptavidin component only, giving a clear indication that LU-10-StrAv localizes to target cells as efficiently as NR-LU-10 whole antibody itself.

EXAMPLE VII

Three-Step Pretargeting

A patient presents with ovarian cancer. A monoclonal antibody (MAb) directed to an ovarian cancer cell antigen is conjugated to biotin to form aMAb-biotin conjugate. The MAb-biotin conjugate is administered to the patient in an amount in excess of the maximum tolerated dose of conjugate administerable in a targeted, chelate labeled molecule protocol (e.g., administration of monoclonal antibody-chelate-radionuclide conjugate) and is permitted to localize to target cancer cells for 24-48 hours. Next, an amount of avidin sufficient to clear non-targeted MAb-biotin conjugate and to bind to the targeted biotin is administered. A biotin-radionuclide chelate conjugate of the type discussed in Example V(A) above is dispersed in a pharmaceutically acceptable diluent and administered to the patient in a therapeutically effective dose. The biotin-radionuclide chelate conjugate localizes to the targeted MAb-biotin-avidin moiety or is removed from the patient via the renal pathway.

EXAMPLE VIII

Two-Step Pretargeting

A patient presents with colon cancer. A monoclonal antibody (MAb) directed to a colon cancer cell antigen is conjugated to streptavidin to form a MAb-streptavidin conjugate. The MAb-streptavidin conjugate is administered to the patient in an amount in excess of the maximum tolerated dose of conjugate administerable in a targeted, chelate labeled molecule protocol (e.g., administration of monoclonal antibody-chelate-radionuclide conjugate) and is permitted to localize to target cancer cells for 24-48 hours. A biotin-radionuclide chelate conjugate of the type discussed in Example V(B) above is dispersed in a pharmaceutically acceptable diluent and administered to the patient in a therapeutically effective dose. The biotin-radionuclide chelate conjugate localizes to the targeted MAb-streptavidin moiety or is removed from the patient via the renal pathway.

What is claimed is:

1. A compound of the following formula:

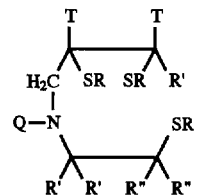

wherein:

each R is a protecting group;

Q is hydrogen or a protecting group;

each T is selected from the group consisting of hydrogen, lower alkyl groups of from 1 to about 6 carbon atoms, electron withdrawing groups, and lower alkyl groups of from 1 to about 6 carbon atoms substituted with electron withdrawing group(s);

each R' is selected from the group consisting of:

—$(CH_2)_n$—COOH with n=0 to about 4,

—$(CH_2)_n$—Z, wherein Z represents a ligand or an anti-ligand selected from the group consisting of avidin, streptavidin and biotin and, optionally further includes a conjungation group which provides for covalent attachment of the ligand or anti-ligand to the —$(CH_2)_n$ moiety and wherein n is 0 to about 4, hydrogen, and a lower alkyl group of from 1 to about 6 carbon atoms;

each R" is selected from the group consisting of:

—$(CH_2)_n$—COOH with n=0 to about 4, hydrogen, and a lower alkyl group of from 1 to about 6 carbon atoms; and the compound comprises at least one —$(CH_2)_n$—Z substituent.

2. The compound of claim 1 wherein one R' or R" substituent is —$(CH_2)_n$—COOH.

3. The compound of claim 1 wherein each T is hydrogen.

4. The compound of claim 1 wherein Q is hydrogen or a methyl group.

5. A compound of claim 1 of the formula:

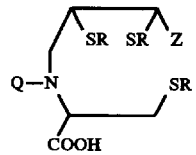

wherein:

each R represents a protecting group;

Q represents hydrogen or a methyl group; and

Z comprises biotin.

6. A compound of the formula:

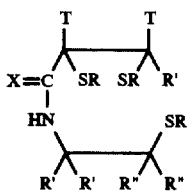

wherein:
each R is a protecting group;
each T is selected from the group consisting of hydrogen, lower alkyl groups of from 1 to about 6 carbon atoms, electron withdrawing groups, and lower alkyl groups of from 1 to about 6 carbon atoms substituted with electron withdrawing group(s);
X is O, S, or NH;
each R' is selected from the group consisting of:
—(CH$_2$)$_n$—COOH with n=0 to about 4,
—(CH$_2$)$_n$—Z, wherein Z represents a ligand or anti-ligand selected from the group consisting of avidin, streptavidin and biotin and, optionally further includes a conjugation group which provides for the covalent attachment of the ligand or anti-ligand to the (CH$_2$)$_n$ group and wherein n is 0 to about 4, hydrogen, and
a lower alkyl group of from 1 to about 6 carbon atoms;
each R" is selected from the group consisting of:
—(CH$_2$)$_n$—COOH with n=0 to about 4,
hydrogen, and
a lower alkyl group of from 1 to about 6 carbon atoms; and
the compound comprises at least one —(CH$_2$)$_n$—Z substituent.

7. The compound of claim 6 wherein one R' or R" substituent is —(CH$_2$)$_n$—COOH.

8. The compound of claim 6 wherein each T is hydrogen.

9. The compound of claim 6 wherein X is O.

10. A compound of claim 6 of the formula:

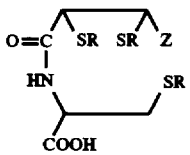

wherein each R is a protecting group and Z comprises biotin.

11. A radionuclide metal chelate-containing compound of the formula:

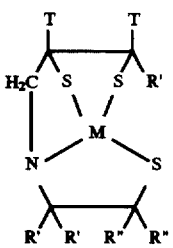

wherein:
M represents a radionuclide metal or oxide thereof;
each T is selected from the group consisting of hydrogen, lower alkyl groups of from 1 to about 6 carbon atoms, electron withdrawing groups, and lower alkyl groups of from 1 to about 6 carbon atoms substituted with electron withdrawing group(s);
each R' is selected from the group consisting of:
—(CH$_2$)$_n$—COOH with n=0 to about 4,
—(CH$_2$)$_n$—Z, wherein Z represents a ligand or an anti-ligand selected from the group consisting of avidin, streptavidin, and biotin and, optionally further includes a conjugation group which provides for the covalent attachment of the ligand or anti-ligand to the (CH$_2$)$_n$ group and wherein n is 0 to about 4, hydrogen, and
a lower alkyl group of from 1 to about $_6$ carbon atoms;
each R" is selected from the group consisting of:
—(CH$_2$)$_n$—COOH with n=0 to about 4,
hydrogen, and
a lower alkyl group of from 1 to about 6 carbon atoms; and
the compound comprises at least one —(CH$_2$)$_n$—Z substituent.

12. A radionuclide metal chelate-containing compound of the formula:

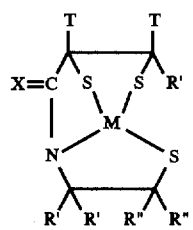

wherein:
M represents a radionuclide metal or oxide thereof;
each T is selected from the group consisting of hydrogen, lower alkyl groups of from 1 to about 6 carbon atoms, electron withdrawing groups, and lower alkyl groups of from 1 to about 6 carbon atoms substituted with electron withdrawing group(s);
X represents O, S, or NH;
each R' is selected from the group consisting of:
—(CH$_2$)$_n$—COOH with n=0 to about 4,
—(CH$_2$)$_n$—Z, wherein Z represents a ligand or an anti-ligand selected from the group consisting of avidin streptavidin and biotin and, optionally further includes a conjugation group which provides for the covalent attachment of the ligand or anti-ligand to the (CH$_2$)$_n$ and wherein n is 0 to about 4, hydrogen, and
a lower alkyl group of from 1 to about 6 carbon atoms;
each R" is selected from the group consisting of:
—(CH$_2$)$_n$—COOH with n=0 to about 4,
hydrogen, and
a lower alkyl group of from 1 to about 6 carbon atoms; and
the compound comprises at least one —(CH$_2$)$_n$—Z substituent.

13. The compound of claim 12, wherein X is O.

14. The compound of claim 13 wherein the radionuclide metal is selected from the group consisting of $^{99m}$Tc, $^{188}$Re, and $^{186}$Re.

15. The compound of claim 13 wherein R' or R" substituent is —(CH$_2$)$_n$—COOH.

16. The compound of claim 13 wherein T is hydrogen.

17. An S$_3$N-biotin conjugate selected from the group consisting of N-methyl-N-[4-biocytinamido-(S,S'-isopropylidene)-2,3-dimercapto]butyryl-S-benzyl cysteine; N-[[(5-biotinamido)-pentylamido]-S,S'-(isopropylidene)-2,3-dimercapto]butyryl-S-benzyl cysteine; biocytinamido-(S-benzyl)-cysteinyl-[S,S'-isopropylidene)-2,3-dimercaptosuccinate; and (S-benzyl)-cysteinyl-[5-biotinamido)-pentylamido]-(S,S'-isopropylidene)-2,3-dimercaptosuccinate.

\* \* \* \* \*